(12) United States Patent
Hamada

(10) Patent No.: US 8,968,656 B2
(45) Date of Patent: Mar. 3, 2015

(54) SAMPLE ANALYZER AND NON-TRANSITORY STORAGE MEDIUM

(75) Inventor: Yuichi Hamada, Kobe (JP)

(73) Assignee: Sysmex Corporation, Kobe (JP)

(*) Notice: Subject to any disclaimer, the term of this patent is extended or adjusted under 35 U.S.C. 154(b) by 0 days.

(21) Appl. No.: 13/074,490

(22) Filed: Mar. 29, 2011

(65) Prior Publication Data

US 2011/0244557 A1  Oct. 6, 2011

(30) Foreign Application Priority Data

Mar. 30, 2010 (JP) ................. 2010-078997

(51) Int. Cl.
*G01N 35/00* (2006.01)
*G01N 35/04* (2006.01)
*B01L 3/00* (2006.01)
*G01N 35/10* (2006.01)

(52) U.S. Cl.
CPC ...... *G01N 35/04* (2013.01); *G01N 2035/00316* (2013.01); *B01L 3/523* (2013.01); *B01L 3/527* (2013.01); *B01L 2200/14* (2013.01); *B01L 2200/145* (2013.01); *B01L 2200/16* (2013.01); *B01L 2300/02* (2013.01); *G01N 35/1002* (2013.01); *G01N 2035/0405* (2013.01)
USPC .......................................................... 422/65

(58) Field of Classification Search
CPC ............. G01N 2035/00316; G01N 35/00732; B01L 3/527; B01L 2200/145
See application file for complete search history.

(56) References Cited

U.S. PATENT DOCUMENTS

| 2005/0123445 | A1* | 6/2005 | Blecka et al. ............ 422/64 |
| 2008/0063570 | A1* | 3/2008 | Fujino et al. ............ 422/99 |
| 2014/0098252 | A1* | 4/2014 | Chang et al. ......... 348/207.99 |

FOREIGN PATENT DOCUMENTS

| JP | 7-159414 A | 6/1995 |
| JP | 9-196925 A | 7/1997 |
| JP | 2003-083998 A | 3/2003 |
| JP | 2004-062767 A | 2/2004 |
| JP | 2008-216173 A | 9/2008 |

* cited by examiner

*Primary Examiner* — P. Kathryn Wright
(74) *Attorney, Agent, or Firm* — Brinks Gilson & Lione

(57) ABSTRACT

A sample analyzer comprising: a container set section in which a reagent container can be set which contains a reagent to be used in a sample analysis; a cover capable of making the container set section be in an open state and a closed state; a locking mechanism capable of permitting and prohibiting a closing of the cover; and a controller that controls the permission and prohibition of the closing of the cover by the locking mechanism. Also a non-transitory storage medium.

15 Claims, 17 Drawing Sheets

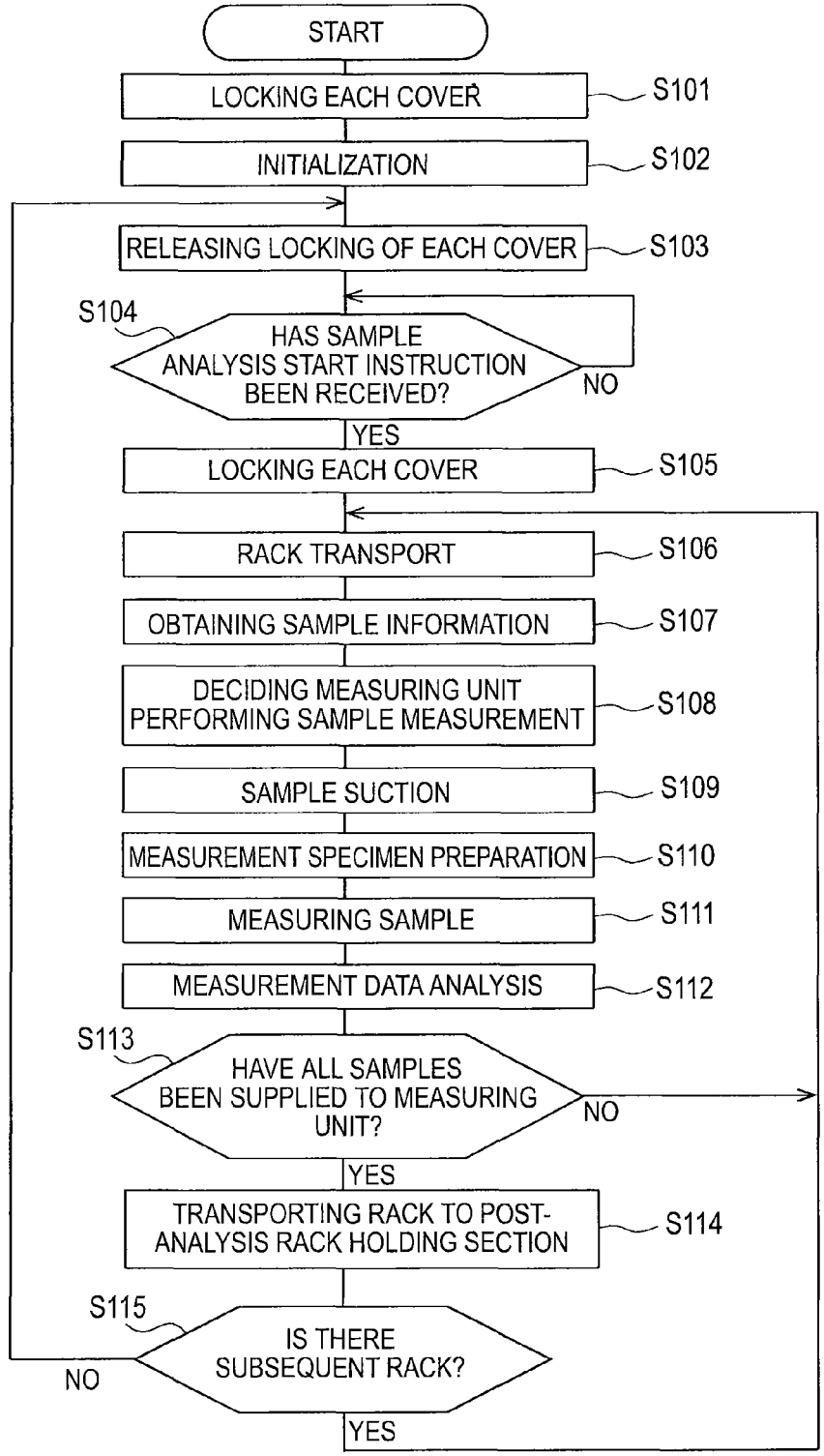

SAMPLE ANALYZER AND NON-TRANSITORY STORAGE MEDIUM

RELATED APPLICATIONS

This application claims priority under 35 U.S.C. §119 to Japanese Patent Application No. 2010-078997 filed on Mar. 30, 2010, the entire content of which is hereby incorporated by reference.

BACKGROUND OF THE INVENTION

1. Field of the Invention

The present invention relates to a sample analyzer which analyzes a sample by using a reagent, and a non-transitory storage medium.

2. Description of the Related Art

There has been known a sample analyzer which suctions a reagent from a reagent container within the sample analyzer, and analyzes a sample by using the reagent. Japanese Laid-Open Patent Publication No. 2008-216173 discloses an automatic analyzer including a reagent box, a lid which is disposed so as to be openable and closable on the upper surface of the reagent box, and a locking mechanism for maintaining a state in which the lid closes the reagent box. When receiving a measurement start instruction from a user, the automatic analyzer locks the lid to maintain the state in which the lid closes the reagent box and starts the measurement operation. When the user replaces a reagent container, this automatic analyzer receives an instruction to temporarily stop the measurement operation from the user, then temporarily stops the measurement operation, and unlocks the lid of the reagent box. After the replacement of the reagent container by the user, when receiving an instruction to re-start the measurement operation from the user, the automatic analyzer checks whether the lid is correctly closed. When determining that the lid is correctly closed, the automatic analyzer locks the lid again and re-starts the measurement operation.

However, in the automatic analyzer disclosed in the above-described Japanese Laid-Open Patent Publication No. 2008-216173, it is possible to close the lid even when the reagent container has been replaced with a reagent container containing an incorrect type of reagent or a reagent container containing a reagent which is not suitable for analysis. When the lid is correctly closed, the lid is locked and the measurement operation is re-started. In such a case, the user is required to again give an instruction to temporarily stop the measurement to the automatic analyzer in order to unlock the lid and re-start the replacement of the reagent container.

SUMMARY OF THE INVENTION

The scope of the present invention is defined solely by the appended claims, and is not affected to any degree by the statements within this summary.

According to a first aspect of the present invention,
a sample analyzer comprising:
a container set section in which a reagent container can be set which contains a reagent to be used in a sample analysis;
a cover capable of making the container set section be in an open state and a closed state;
a locking mechanism capable of permitting and prohibiting a closing of the cover; and
a controller that controls the permission and prohibition of the closing of the cover by the locking mechanism.

According to a second aspect of the present invention,
at least one non-transitory storage medium which stores programs executable collectively by at least one processor to:
prohibit a closing of a cover of a container set section in which a reagent container can be set which contains a reagent to be used in a sample analysis;
determine whether a predetermined condition is satisfied; and
permit the closing of the cover if the predetermined condition is satisfied.

BRIEF DESCRIPTION OF THE DRAWINGS

FIG. 13 is a flowchart showing the procedures of a sample analysis control process of the information processing unit according to the embodiment.

DETAILED DESCRIPTION OF THE PREFERRED EMBODIMENTS

Hereinafter, embodiments of the present invention will be described on the basis of the drawings.

[Configuration of Sample Analyzer]

Figure 1:
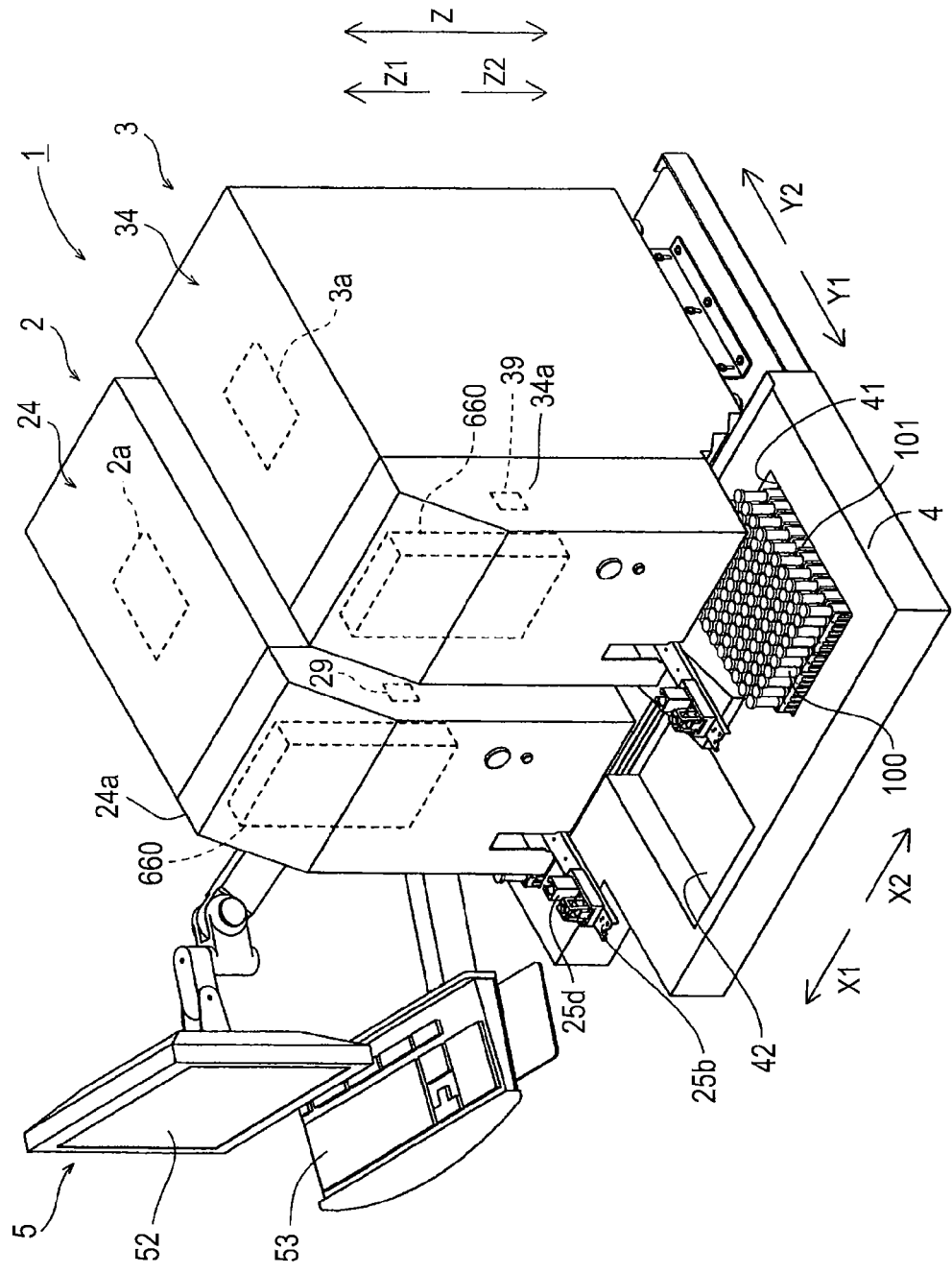
FIG. 1 is a perspective view showing the entire configuration of a sample analyzer according to an embodiment.

FIG. 1 is a perspective view showing the entire configuration of a sample analyzer according to this embodiment. The sample analyzer 1 according to this embodiment is a multiple blood cell analyzer which classifies blood cells contained in a blood sample into white blood cells, red blood cells, platelets and the like and counts the number for each kind of blood cell. As shown in FIG. 1, the sample analyzer 1 according to this embodiment includes two measuring units, which are a first measuring unit 3 disposed in the direction of the arrow X2 and a second measuring unit 2 disposed in the direction of the arrow X1, a sample transport unit (sampler) 4 which is disposed in front of the first measuring unit 3 and the second measuring unit 2 (in the direction of the arrow Y1) and an information processing unit 5 which is composed of a personal computer (PC) electrically connected to the first measuring unit 3, the second measuring unit 2 and the sample transport unit 4. In addition, the sample analyzer 1 is connected to a host computer 6 (see FIG. 2) by the information processing unit 5.

<Configuration of Measuring Units>

Figure 2:
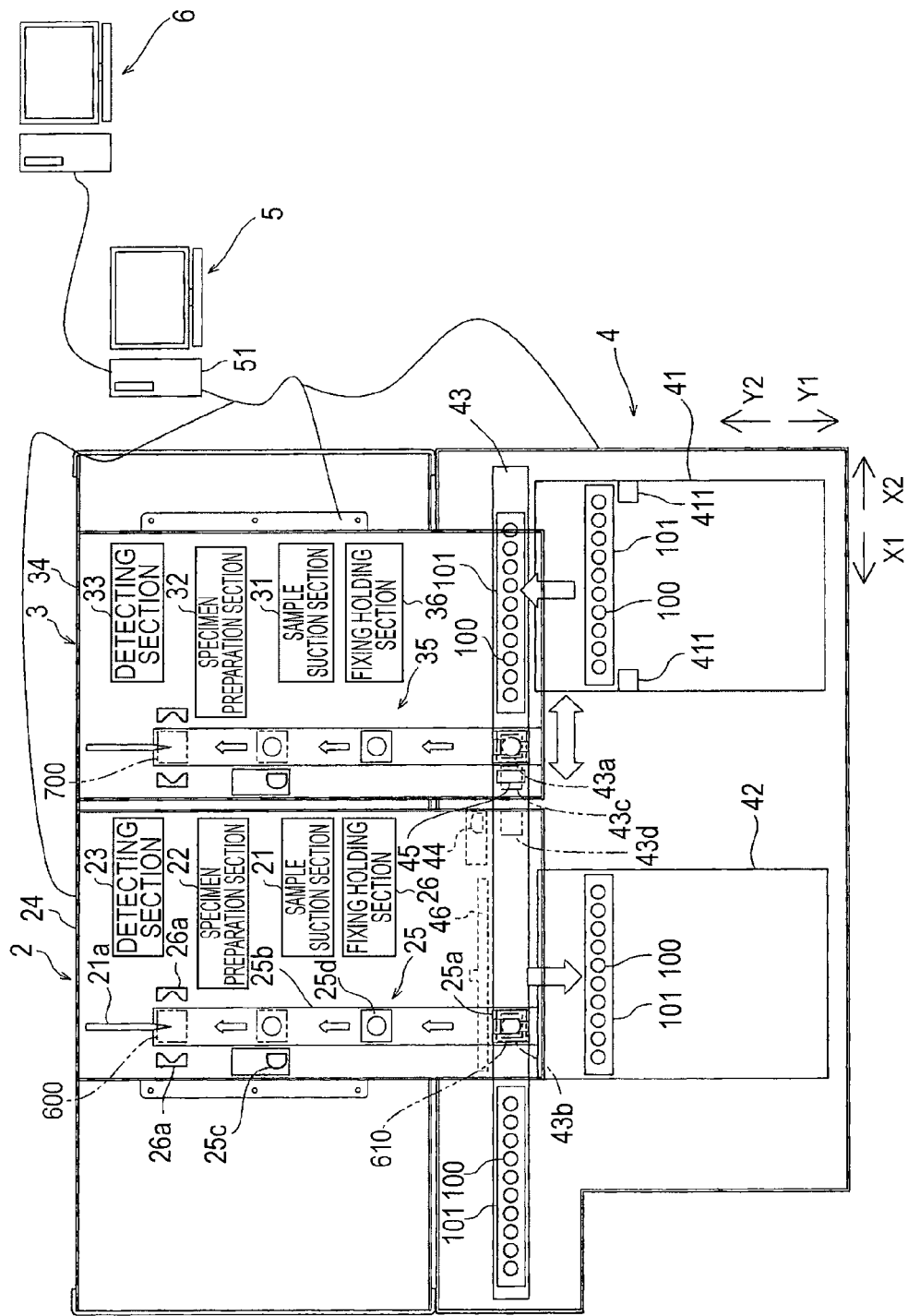
FIG. 2 is a schematic view showing the configuration of the sample analyzer according to the embodiment.

FIG. 2 is a schematic view showing the configuration of the sample analyzer 1 according to this embodiment. As shown in FIGS. 1 and 2, the first measuring unit 3 and the second measuring unit 2 are substantially the same kind of the measuring units and are disposed next to each other. In greater detail, in this embodiment, the second measuring unit 2 uses the same measurement principle as that of the first measuring unit 3 and measures a sample relative to the same measurement item. Further, the second measuring unit 2 also measures a measurement item which is not analyzed by the first measuring unit 3. In addition, as shown in FIG. 2, the second measuring unit 2 and the first measuring unit 3 have sample suction sections 21 and 31 which suction blood which is a sample from a sample container 100, specimen preparation sections 22 and 32 which prepare a measurement specimen from the blood suctioned by the sample suctions sections 21 and 31, and detecting sections 23 and 33 which detect blood cells in the blood from the measurement specimen prepared by the specimen preparation sections 22 and 32, respectively. As shown in FIG. 1, in the first measuring unit 3 and the second measuring unit 2, driver substrates 3a and 2a are provided to drive actuators for the mechanism sections and receive a detection signal from a sensor, respectively.

In addition, as shown in FIG. 2, the second measuring unit 2 and the first measuring unit 3 include unit covers 24 and 34 which accommodate therein the sample suction sections 21 and 31, the specimen preparation sections 22 and 32 and the like, sample container transport sections 25 and 35 which take sample containers 100 into the unit covers 24 and 34 and transport the sample containers 100 up to suction positions 600 and 700 at which the sample suction sections 21 and 31 perform a suction operation, and fixing holding sections 26 and 36 which fix and hold sample containers 100 at the suction positions 600 and 700, respectively. Since the first measuring unit 3 and the second measuring unit 2 are substantially the same kind of the measuring units as described above, the second measuring unit 2 will be described hereinbelow and the description for the first measuring unit 3 will be omitted.

Figure 3:
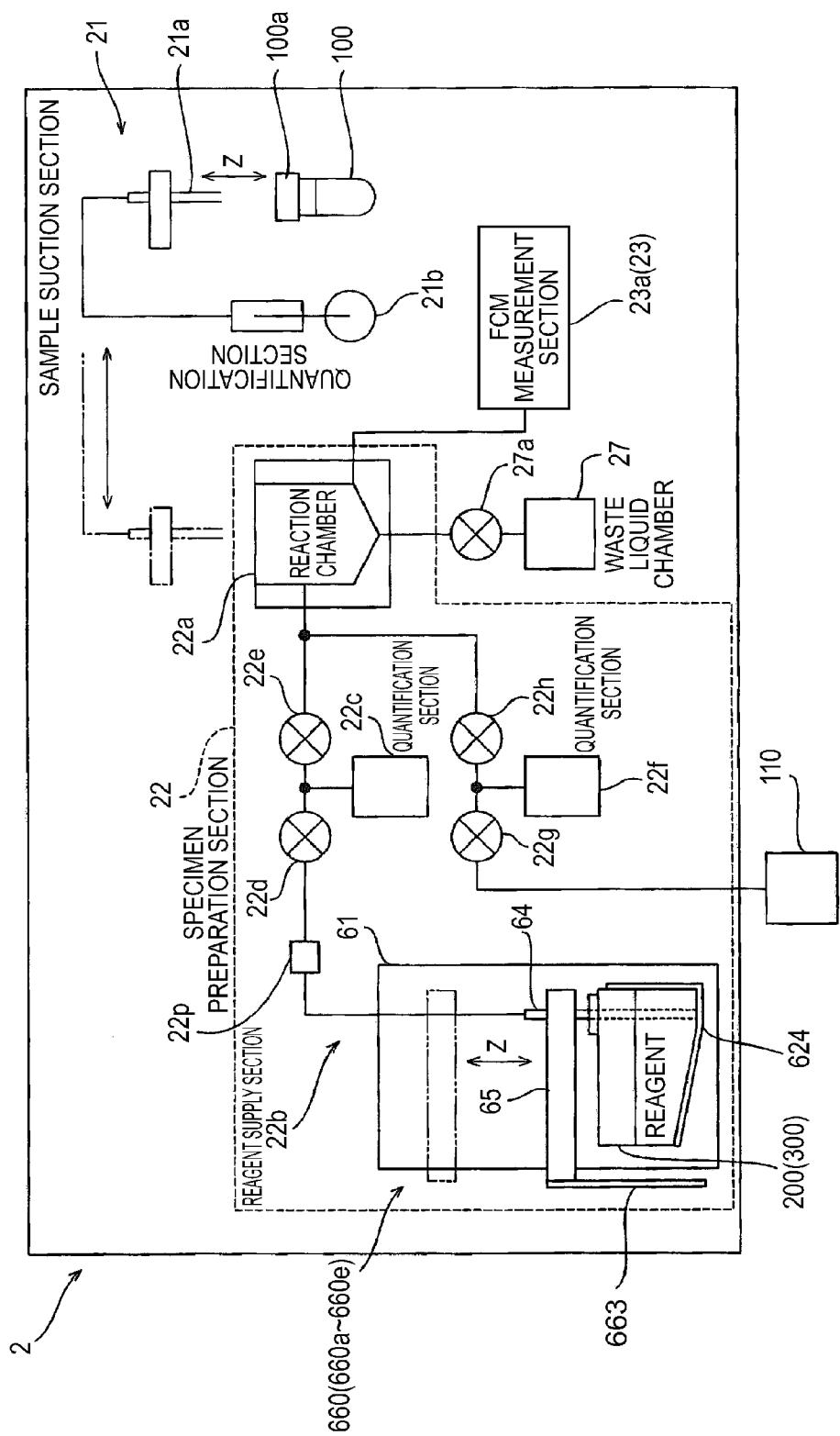
FIG. 3 is a schematic view showing the configuration of a measuring unit according to the embodiment.

FIG. 3 is a schematic view showing the configuration of the second measuring unit according to this embodiment. As shown in FIG. 3, the sample suction section 21 has a piercer 21a which is a suction tube through which a reagent passes and a quantification section 21b. The piercer 21a is formed so that the tip end thereof can penetrate (puncture) a sealing lid 100a to be described later of a sample container 100. In addition, the piercer 21a is configured to be moved in the vertical direction (Z direction) by a piercer driving section (not shown) and to be moved up to a reaction chamber 22a to be described later. The quantification section 21b is composed of a syringe pump or the like and has a function of suctioning and discharging a predetermined amount of sample from a sample container 100 via the piercer 21a. Accordingly, a predetermined amount of sample necessary for sample measurement is suctioned from a sample container 100 and can be supplied to the reaction chamber 22a.

The detecting section 23 performs RBC detection (detection of red blood cells) and PLT detection (detection of platelets) by a sheath flow DC detection method and performs HGB detection (detection of hemoglobin in blood) by an SLS-hemoglobin method. In addition, as shown in FIG. 3, the detecting section 23 has an FCM measurement section 23a which performs WBC detection (detection of white blood cells) by a flow cytometry method using semiconductor laser. In addition, the detection result obtained by the measuring section 23 is transmitted to the information processing unit 5 as measurement data (measurement result) of the sample. The FCM measurement section 23a is configured to irradiate a measurement specimen which is prepared by the specimen preparation section 22 to be described later with light from the semiconductor laser, detect scattered light and fluorescence generated from the components in the measurement specimen and output a scattered light signal and a fluorescence signal obtained.

As shown in FIG. 3, the specimen preparation section 22 of the second measuring unit 2 has the reaction chamber 22a and a reagent supply section 22b connected to the reaction chamber 22a. The reaction chamber 22a is configured to mix and react a sample (blood) suctioned by the sample suction section 21 and a reagent supplied from the reagent supply section 22b together. A plurality of the reaction chambers 22a is provided in accordance with the kind of the measurement. The reaction chambers 22a are each supplied with plural kinds of reagents (staining liquid and the like) according to the measurement items, respectively, and measurement specimens according to the various measurement items are prepared through the sample-reagent mixing and reaction process. The prepared measurement specimen is supplied to the FCM measurement section 23a.

In this embodiment, the reagent supply section 22b is provided in the unit cover 24 and has a reagent container holder 660 which holds a plurality of reagent containers 200 (see FIG. 9) or 300 (see FIG. 10) each containing a predetermined amount of reagent. In such a reagent container holder 660, a piercer 64 is provided to suction the reagent in the reagent container 200 (or 300). In addition, the reagent supply section 22b has a bubble sensor 22p, a quantification section 22c including a syringe pump and a diaphragm pump and electromagnetic valves 22d and 22e which open and close the flow passage when a suctioned reagent is transferred to the quantification section 22c and the reaction chamber 22a. As shown in FIG. 3, the bubble sensor 22p is provided in the flow passage between the piercer 64 and the reaction chamber 22a to detect bubbles which are included in the liquid suctioned from the piercer 64. Further, in addition to the reagent containers 200 (or 300) which are held in the reagent container holder 660, the reagent supply section 22b has a quantification section 22f for transferring reagents (hemolytic agent and the like) from a large capacity reagent container 110, disposed outside the measuring unit, and electromagnetic valves 22g and 22h. The reagent containers 200 and 300 will be described later in detail.

As shown in FIG. 1, an openable and closable front cover 24a is provided on the front side of the unit cover 24. The reagent container holder 660 is disposed in an upper front portion of the second measuring unit 2 and is exposed to the outside by opening the front cover 24a. Accordingly, a user can easily replace the reagent containers 200 and 300. In addition, an openable and closable front cover 34a is also provided on the front side of the unit cover 34 of the first measuring unit 3. Similarly, the reagent container holder 660 is disposed in an upper front portion of the first measuring unit 3 and is exposed to the outside by opening the front cover 34a.

In addition, the first measuring unit 3 and the second measuring unit 2 are provided with buzzers 39 and 29 emitting an alarm sound, respectively. The buzzers 39 and 29 are connected to the driver substrates 3a and 2a, respectively, and emit an alarm sound by a control signal of the information processing unit 5.

Figure 4:
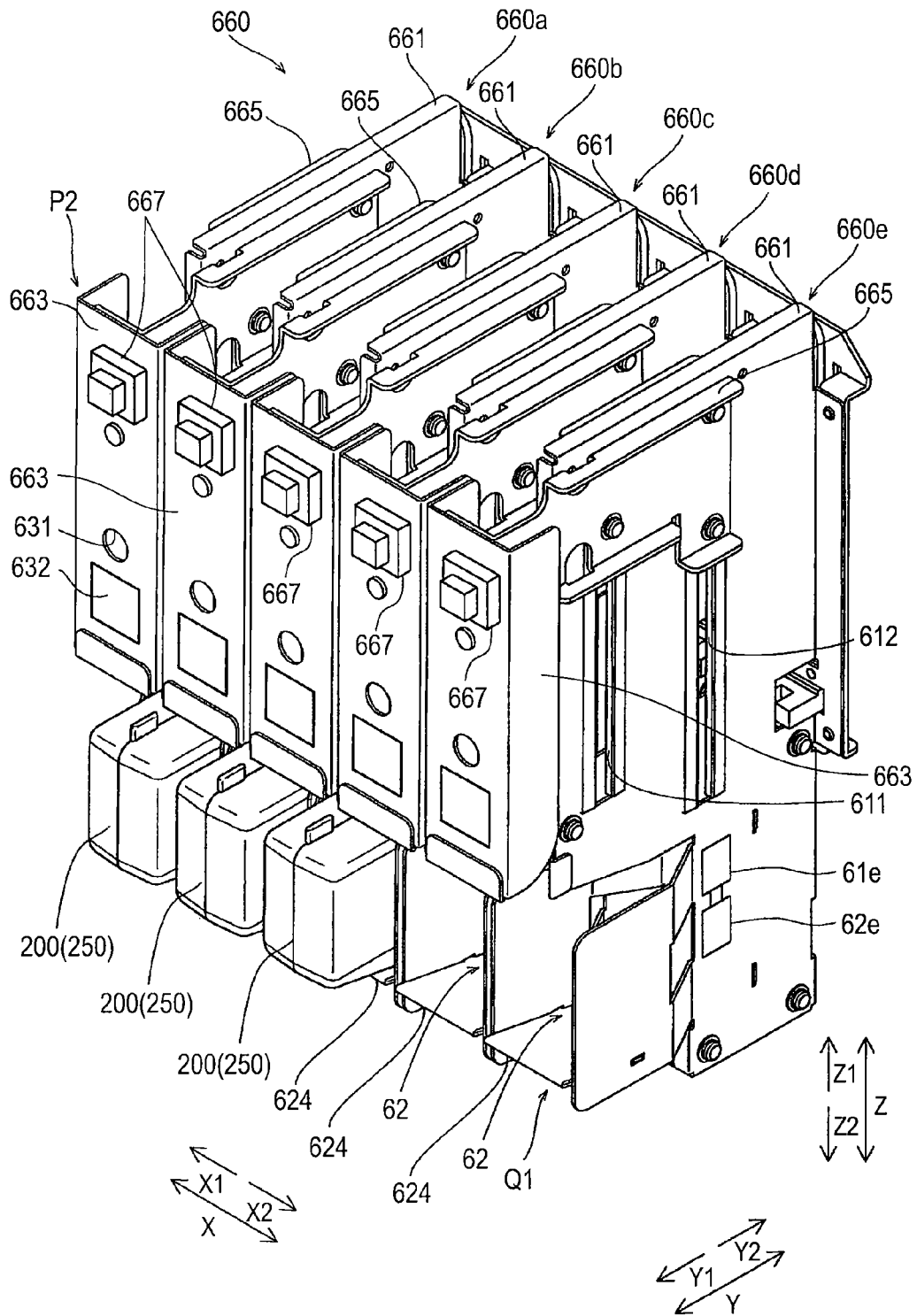
FIG. 4 is a perspective view showing the configuration of a reagent container holder of the measuring unit according to the embodiment.
Figure 5:
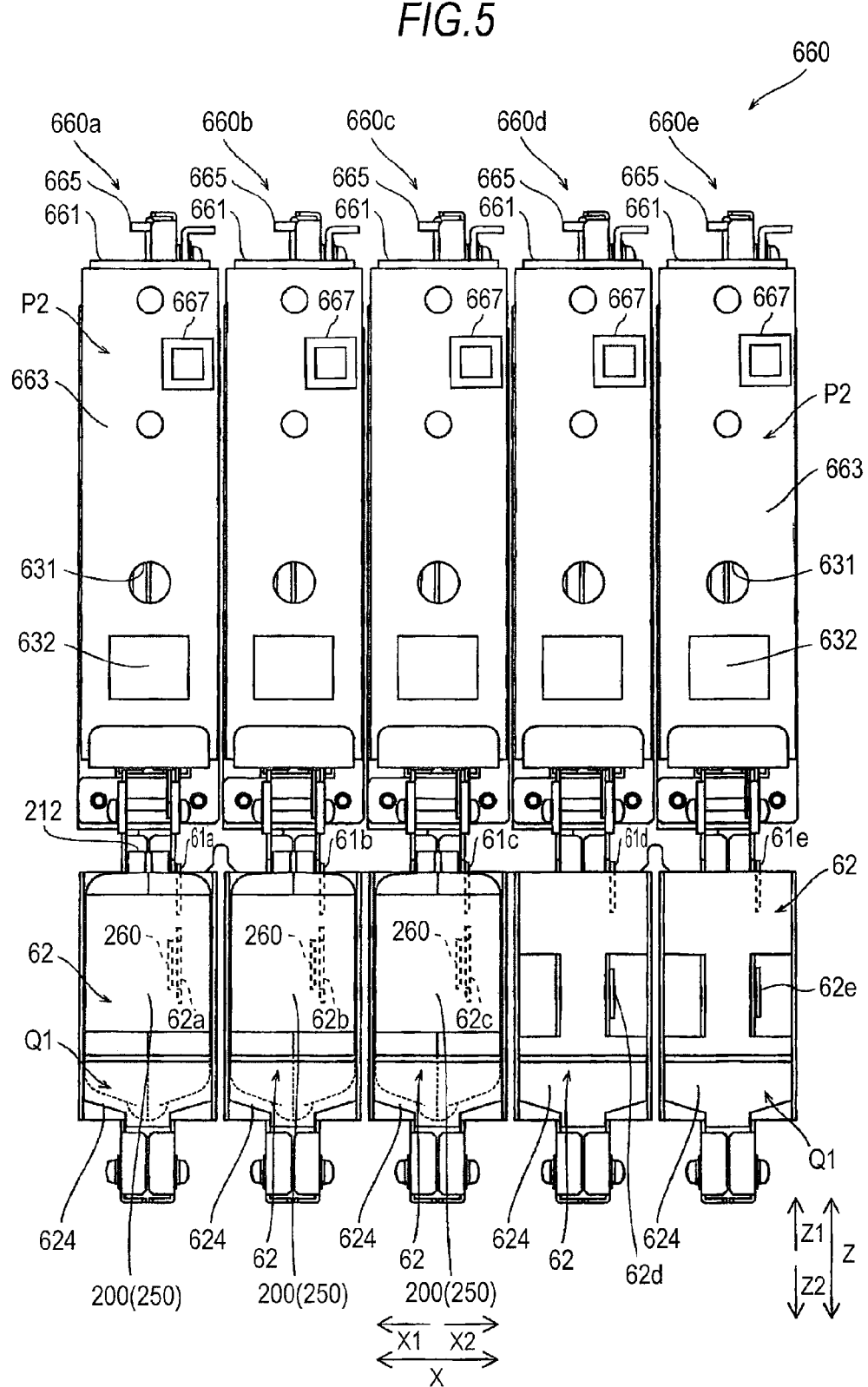
FIG. 5 is a front view showing the configuration of the reagent container holder of the measuring unit according to the embodiment.

Next, the configuration of the reagent container holder 660 will be described in detail. FIGS. 4 and 5 are a perspective view and a front view showing the configuration of the reagent container holder of the second measuring unit according to this embodiment, respectively. As shown in FIGS. 4 and 5, the reagent container holder 660 has five holder sections 660a, 660b, 660c, 660d and 660e and is configured to hold total five (five kinds) reagent containers 200 (or 300). The reagent containers 200 (or 300) which are held in the reagent container holder 660 contain different kinds of reagents (staining liquid) for measuring a plurality of measurement items by the FCM measuring section 23a, respectively. As the reagent container, the reagent container 200 (see FIG. 9) having a large size (about 100 mL) and the reagent container 300 (see FIG. 10) having a small size (about 20 mL) are used in accordance with the kinds of the reagents and the holder sections 660a to 660e are configured to hold any of the reagent containers 200 and 300. That is, the five holder sections 660a to 660e have similar configurations. In the three holder sections 660a to 660c, the reagent containers 200 having a large size are set, and in the two holder sections 660d and 660e, the reagent containers 300 having a small size (not shown in FIGS. 4 and 5) are set. In greater detail, the reagent containers 200 each containing a staining liquid for sub-class classification of white blood cells are installed in the holder sections 660a to 660c. The reagent container 300 containing a staining liquid for detection of reticulocytes is installed in the holder section 660d and the reagent container 300 containing a staining liquid for detection of platelets is installed in the holder section 660e. Each of the holder sections 660a to 660e has a chassis 661, a reagent container installation section 62, a cover 663 for opening and closing the reagent container installation section 62, the above-described piercer 64, and a piercer lifting mechanism 665. A pressing button switch 667 is attached to the front surface of each cover 663.

In the holder sections 660a to 660e, radio frequency identification (RFID) readers 61a to 61e and antennas 62a to 62e which are connected to the RFID readers 61a to 61e, respectively, in association therewith are provided. In each of the reagent containers 200 and 300, an RFID tag 260 (360) is attached which stores various information related to the reagent. The RFID tags 260 (360) are passive tags not needing a battery and are driven by radio waves sent from the antennas 62a to 62e. The RFID tag 260 (360) stores information such as a reagent code indicating the kind of the reagent, an expiration date of the reagent, the maximum number of uses of the reagent, a serial number individually assigned to each reagent, a lot number and an expiry date after opening. When reading reagent information from the RFID tag 260 (360), the RFID readers 61a to 61e send radio waves from the antennas 62a to 62e. When the radio waves are sent from the antennas 62a to 62e, they are partially reflected by the RFID tag 260 (360). The reagent information stored in the RFID tag 260 (360) is put on the reflected wave. The antennas 62a to 62e receive the reflected wave from the RFID tag 260 (360) and the RFID readers 61a to 61e obtain the reagent information included in this reflected wave.

The reagent container installation section 62 is provided in the lower portion of the chassis 661 (see FIG. 5) and has an inner space which is provided for installing a reagent container 200 (300).

Figure 6:
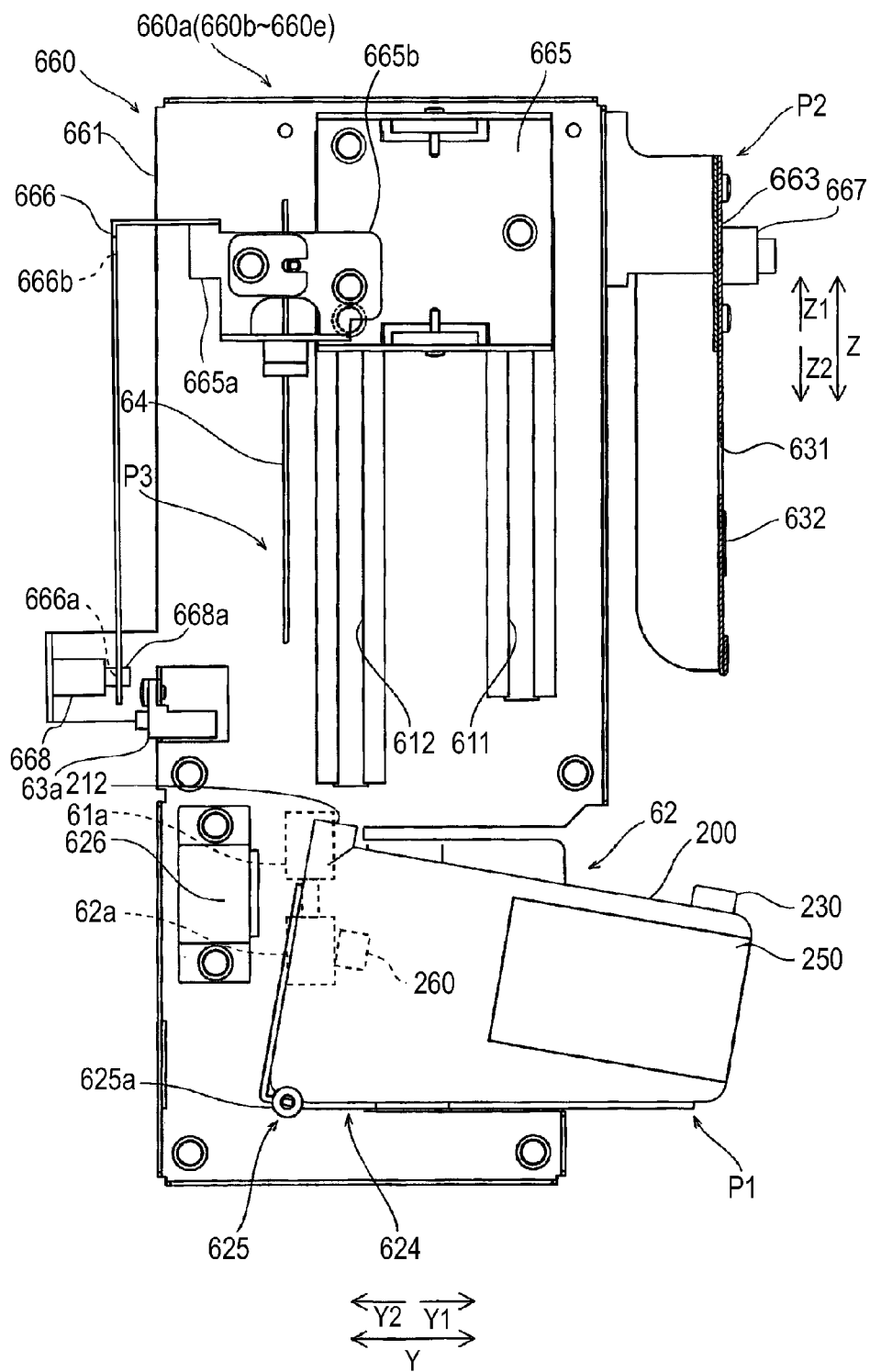
FIG. 6 is a vertical cross-sectional view showing the internal configuration of the reagent container holder according to the embodiment.
Figure 7:
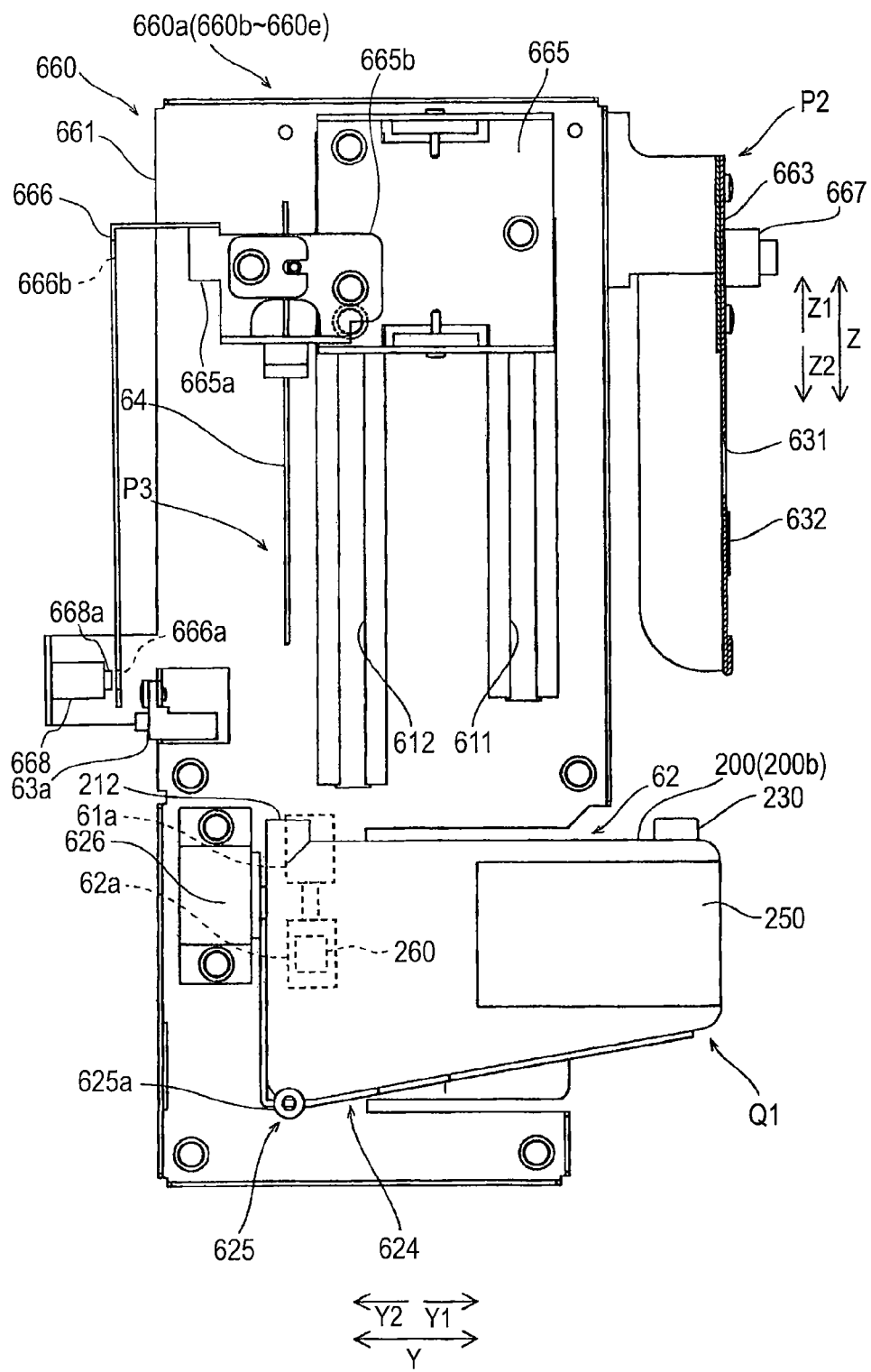
FIG. 7 is a vertical cross-sectional view showing the internal configuration of the reagent container holder according to the embodiment.
Figure 8:
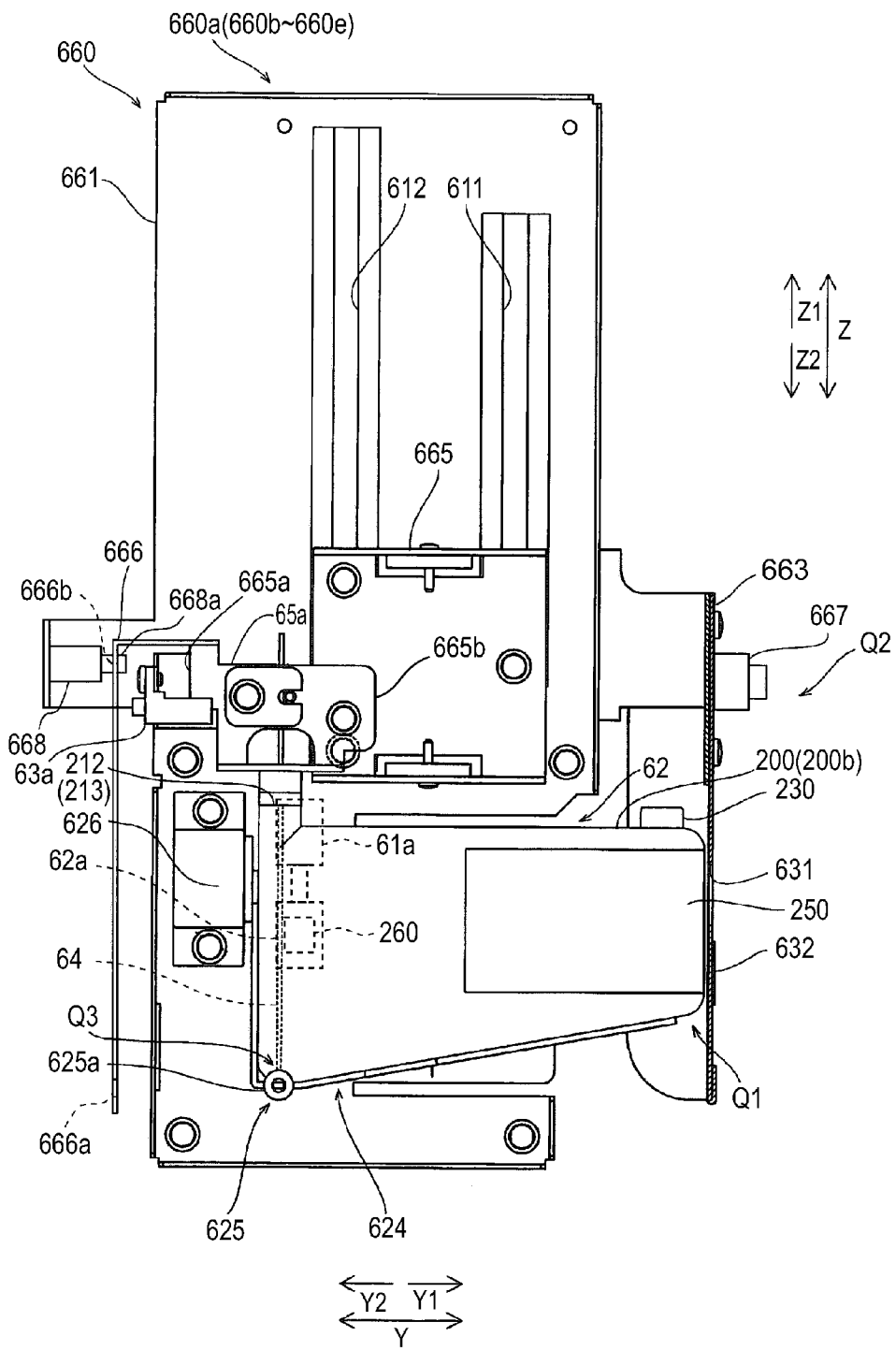
FIG. 8 is a vertical cross-sectional view showing the internal configuration of the reagent container holder according to the embodiment.

FIGS. 6 to 8 are vertical cross-sectional views schematically showing the internal configuration of the reagent container holder according to this embodiment. FIG. 6 shows a state in which a reagent container is attached or removed in the reagent container holder. FIG. 7 shows a state in which a reagent container is set in the reagent container holder. FIG. 8 shows a state in which the cover of the reagent container holder is lowered. As shown in FIG. 6, the reagent container installation section 62 has a support section 624 which supports a reagent container 200 (300) and a rotation mechanism 625 which rotatably supports the support section 624. The support section 624 is formed to have a shape corresponding to the shape of a reagent container 200 (300) and is brought into contact with the front and lower surfaces of the reagent container 200 (300). The rotation mechanism 625 is configured to rotate the support section 624 around a bearing 625a provided near the bent portion of the support section 624.

Further, in the chassis 661, an engaging section 626 is provided which engages with the rotating support section 624 through the contact with the support section 624. The engaging section 626 is provided with a magnet and adheres to the front portion of the support section 624 using a magnetic force. Accordingly, the support section 624 is configured to move between a placement position P1 (see FIG. 6) on which the lower surface of a reagent container 200 (300) is made horizontal and a setting position Q1 (see FIG. 7) at which the front and rear end surfaces of a reagent container 200 (300) are made vertical. An opening section 212 (312) to be described later of a reagent container 200 (300) is made horizontal and is positioned immediately below the piercer 64 in a state in which the reagent container is disposed at this setting position Q1 as shown in FIG. 7.

Each of the antennas 62a to 62e is attached to the side portion of each reagent container installation section 62. When a reagent container 200 (300) is positioned at the setting position Q1, the RFID tag 260 (360) of the reagent container 200 (300) is disposed next to the antennas 62a to 62e in the reagent container installation section 62 in which the reagent container 200 (300) is installed. Accordingly, the reflected wave from the RFID tag 260 (360) of the reagent container 200 (300) installed in the reagent container installation section 62 is received by the nearest of the antennas 62a to 62e (that is, the one disposed next to the tag). The reflected wave sent from the RFID tag 260 (360) is very weak and is not received by the other antennas other than the nearest antenna.

As shown in FIG. 6, the cover 663 is disposed on the front side of each of the holder sections 660a to 660e (chassis 661) (in the direction of the arrow Y1) and is attached to the piercer lifting mechanism 665. The cover 663 is configured to be moved between a lifting position P2 (see FIG. 7) related to opening of the reagent container installation section 62 and a lowered position Q2 (see FIG. 8) related to covering (closing) of the reagent container installation section 62 by the piercer lifting mechanism 665. In addition, as shown in FIG. 5, a window section 631 composed of an opening is provided at a predetermined position in the cover 663. As shown in FIG. 8, in a state in which the cover 663 is positioned at the lowered position Q2 related to covering (closing) of the reagent container installation section 62, a user can visually confirm a label 250 (350, see FIG. 10) adhered to the reagent container 200 (300) via this window section 631. A mark for identifying the kind of the reagent container 200 (300) (kind of the reagent) is printed at a position which can be visually confirmed via the window section 631 on the label 250 (350). In addition, a label 632, on which a mark is printed for identifying the kind of the reagent container 200 (300) (kind of the reagent) set in the reagent container installation section 62, is adhered to the cover 663. That is, in the five holder sections 660a to 660e, reagent containers 200 (300) each containing a fixed kind of reagent are set, and thus in accordance with this, the labels 632 for identifying the kinds of the reagents to be set are adhered to the covers 663 of the holder sections 660a to 660e, respectively. Accordingly, in a state in which the reagent containers 200 (300) are set in the reagent container installation section 62 (in a state in which the cover 663 is lowered to the lowered position Q2), it is possible to confirm whether the correct reagents are set in the holder sections 660a to 660e from the labels 632 which are adhered to the covers 663 and the labels 250 (350) which are visually confirmed via the window sections 631.

In addition, each of the holder sections 660a to 660e is provided with a cover opening/closing sensor 63a which detects the opening and closing of the corresponding cover 663. The cover opening/closing sensor 63a is a photo-interrupter which has a light-emitting section and a light-receiving section opposed to each other and detects the opening and closing of the cover by detecting a detection piece 665a provided in the piercer lifting mechanism 665. In greater detail, when the cover is at the lowered position Q2, the detection piece 665a is disposed between the light-emitting section and the light-receiving section of the cover opening/closing sensor 63a, and when the light-receiving section detects that the detection piece 665a shields the light from the light-emitting section, the closure of the cover 663 is detected. When the light-receiving section detects the light from the light-emitting section without the shielding by the detection piece 665a, the opening of the cover 663 is detected.

This detection piece 665a is formed using a protruding portion of a support plate 665b supporting the piercer 64 and the support plate 665b continuously extends backward from the upper portion of the detection piece 665a. Further, the support plate 665b is bent downward at the rear portion of the detection piece 665a and the lower side from the bent portion is formed as a locking section 666 having a vertical plate shape. The locking section 666 is provided with a first locking hole 666a near the lower end thereof and a second locking hole 666b near the upper end thereof.

A solenoid support section 661a protrudes backward near the position at which the cover opening/closing sensor 63a of the chassis 661 is attached. Such a solenoid support section 661a is bent by 90 degrees at the tip end and supports a solenoid 668. The solenoid 668 has a rod-shaped plunger 668a and can move the plunger 668a by being driven. The plunger 668a is biased backward by a spring (not shown) built in the solenoid 668. When a current is not supplied to the solenoid 668, the plunger 668a is positioned at a locking release position accommodated in the main body of the solenoid 668. When a current is supplied to the solenoid 668, the plunger 668a moves forward due to an electromagnetic force. The moving end position at the front side of the plunger 668a is referred to as a locking position. That is, the solenoid 668 can displace the plunger 668a between the locking position and the locking release position.

As shown in FIG. 7, the piercer 64 is disposed above the innermost portion (end in the direction of the arrow Y2) of the reagent container installation section 62 and is configured to be moved in the vertical direction (Z direction) by the piercer lifting mechanism 665 holding the piercer 64. The piercer 64 is sharply formed so that the tip end thereof can penetrate (puncture) a sealing material 213 (313) (see FIGS. 9 and 10) for sealing the opening section 212 (312) of the reagent container 200 (300). In addition, as shown in FIG. 3, the upper end of the piercer 64 is connected to the flow passage (omitted in FIGS. 6 to 11) extending to the reaction chamber 22a and the quantification section 22c.

As shown in FIGS. 7 and 8, the piercer lifting mechanism 665 is configured to hold the piercer 64 and the cover 663. In addition, the piercer lifting mechanism 665 engages to be moved in the vertical direction (Z direction) to groove sections 611 and 612 provided in the chassis 661. Accordingly, the piercer lifting mechanism 665 is configured to integrally move the piercer 64 in the vertical direction (Z direction) in conjunction with the opening and closing (lifting and lowering) of the cover 663. In addition, as shown in FIG. 7, in a state in which the cover 663 is disposed at the lifting position P2, the piercer 64 is disposed at a lifting position P3 above the reagent container installation section 62. In addition, as shown in FIG. 8, in a state in which the cover 663 is disposed at the lowered position Q2, the piercer 64 is disposed at a lowered position Q3 near the inner bottom portion immediately below the opening section 212 (312) of the reagent container 200 (300).

When the cover 663 is opened and the piercer 64 is at the lifting position P3, the first locking hole 666a of the locking section 666 is opposed to the solenoid 668. At this time, when the solenoid 668 is driven and the plunger 668a protrudes up to the locking position, the plunger 668a passes through the first locking hole 666a and the locking section 666 is fixed by the solenoid 668. Accordingly, the locking section is locked in a position where the cover 663 is opened (hereinafter, referred to as the "open position"). At this time, the cover 663 cannot be closed.

Meanwhile, when a current is not supplied to the solenoid, the plunger 668a is positioned at the locking release position and the plunger 668a is separated from the first locking hole 666a. Accordingly, the locking section 666 is not locked by the solenoid 668 and can move downward, and thus it can close the cover 663.

When the cover 663 is closed and the piercer 64 is at the lowered position Q3, the second locking hole 666b of the locking section 666 is opposed to the solenoid 668. At this time, when the solenoid is driven and the plunger 668a protrudes up to the locking position, the plunger 668a passes through the second locking hole 666b and the locking section 666 is fixed by the solenoid 668. Accordingly, the locking section is locked in a position where the cover 663 is closed (hereinafter, referred to as the "closed position"). At this time, the cover 663 cannot be opened.

The solenoid 668 can be operated by operating the pressing button switch 667. When a certain cover 663 in the closed position is locked and a user opens this cover 663, the current supply to the solenoid 668 is stopped when the user presses the pressing button switch 667 provided in the cover 663. Accordingly, the plunger 668a is moved to the locking release position and the locking of the cover 663 is released. In this state, the user can open the cover 663.

As shown in FIG. 3, the quantification section 22c is configured to suction a predetermined amount of reagent in a reagent container 200 (300) to the inside of the quantification section 22c via the piercer 64 by opening the electromagnetic valve 22d and closing the electromagnetic valve 22e in a state in which the piercer 64 is disposed at the lowered position Q3 in the reagent container 200 (300) (see FIG. 8). Accordingly, the reagent is quantified in a predetermined amount necessary for the preparation of a measurement specimen. In addition, the quantification section 22c is configured to transfer the reagent quantified in the quantification section 22c to the reaction chamber 22a by closing the electromagnetic valve 22d and opening the electromagnetic valve 22e.

In addition, the quantification section 22f and the electromagnetic valves 22g and 22h which are connected to the large capacity reagent container 110 exteriorly disposed are configured in the same manner. By controlling the operations of these sections, various reagents are transferred to the inside of the reaction chamber 22a. In addition, in the second measuring unit 2, a waste liquid chamber 27 is provided for discarding a specimen on which the measurement has been performed (on which the preparation has been performed), and is configured to discard a specimen on which the measurement has been performed (on which the preparation has been performed) by opening and closing of an electromagnetic valve 27a.

As shown in FIG. 2, the sample container transport section 25 is configured to be linearly moved in the vertical direction (in the direction of the arrows Z1 and Z2) and has a hand section 25a capable of gripping a sample container 100, a sample container transfer section 25b horizontally moving a sample container 100 in the direction of the arrows Y1 and Y2 and a barcode reading section 25c.

The hand section 25a is disposed above a transport passage for a rack 101 which is transported by the sample transport unit 4. In addition, the hand section 25a is configured to move downward (in the direction of the arrow Z2) and then grip a sample container 100 accommodated in the rack 101 when the sample transport unit 4 transports the sample container 100 to a predetermined intake position 43b.

In addition, the hand section 25a can stir the blood in the gripped sample container 100. In addition, after stirring, the hand section sets the sample container 100 in a sample setting section 25d which is moved to a sample setting position 610 by the sample container transfer section 25b. As shown in FIG. 2, the second intake position 43b and the sample setting position 610 are disposed to overlap each other in a planar view.

The sample container transfer section 25b has the sample setting section 25d as shown in FIGS. 1 and 2 and can move the sample setting section 25d to a predetermined position according to the operation of the measurement process. In greater detail, the sample setting section 25d can be disposed at the suction position 600 and the sample setting position 610 shown in FIG. 2 by the sample container transfer section 25b. In addition, as shown in FIG. 1, the sample container transfer section 25b is configured to be moved to a predetermined position which is outside the unit cover 24 so that a user can manually set a sample container 100 when an emergency sample is measured or the sample transport unit 4 is not used.

The barcode reading section 25c is configured to read a barcode (not shown) adhered to each sample container 100. The barcode (not shown) of each sample container 100 is adhered uniquely to each sample and is used in the management of the analysis results of the samples.

The fixing holding section 26 is configured to fix and hold a sample container 100 transferred to the suction position 600. In greater detail, as shown in FIG. 2, the fixing holding section 26 has a pair of chucks 26a and is configured to grip a sample container 100 by moving the pair of chucks 26a to be close to each other.

Next, the reagent containers 200 and 300 will be described in detail which are used in the second measuring unit 2 and the first measuring unit 3 according to this embodiment and are set in the reagent container holders 660.

Figure 9:
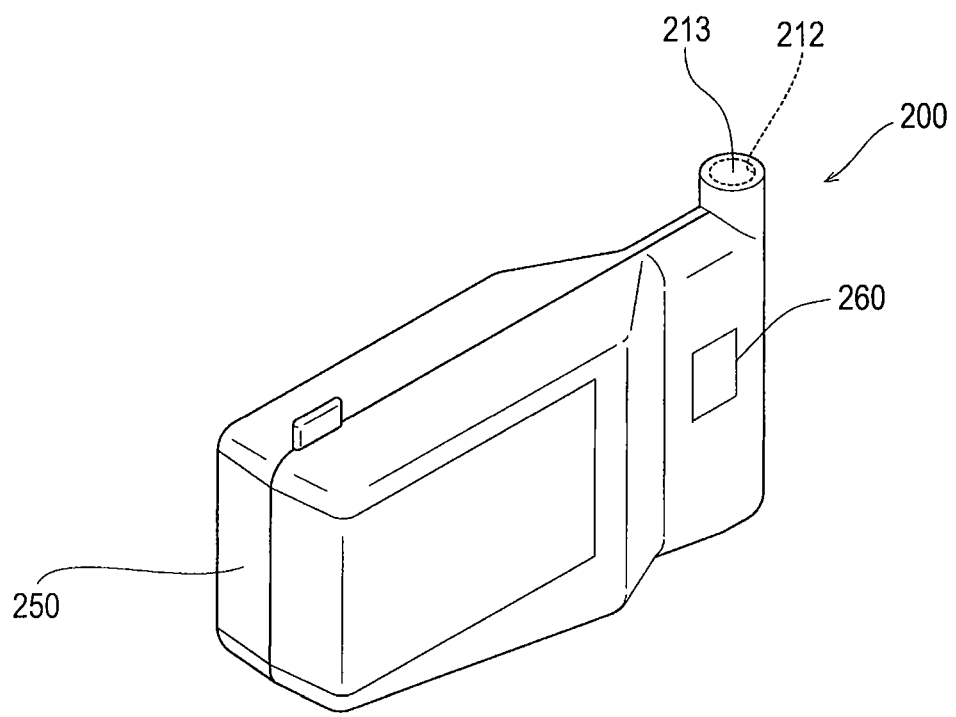
FIG. 9 is a perspective view showing the configuration of a reagent container according to the embodiment.
Figure 10:
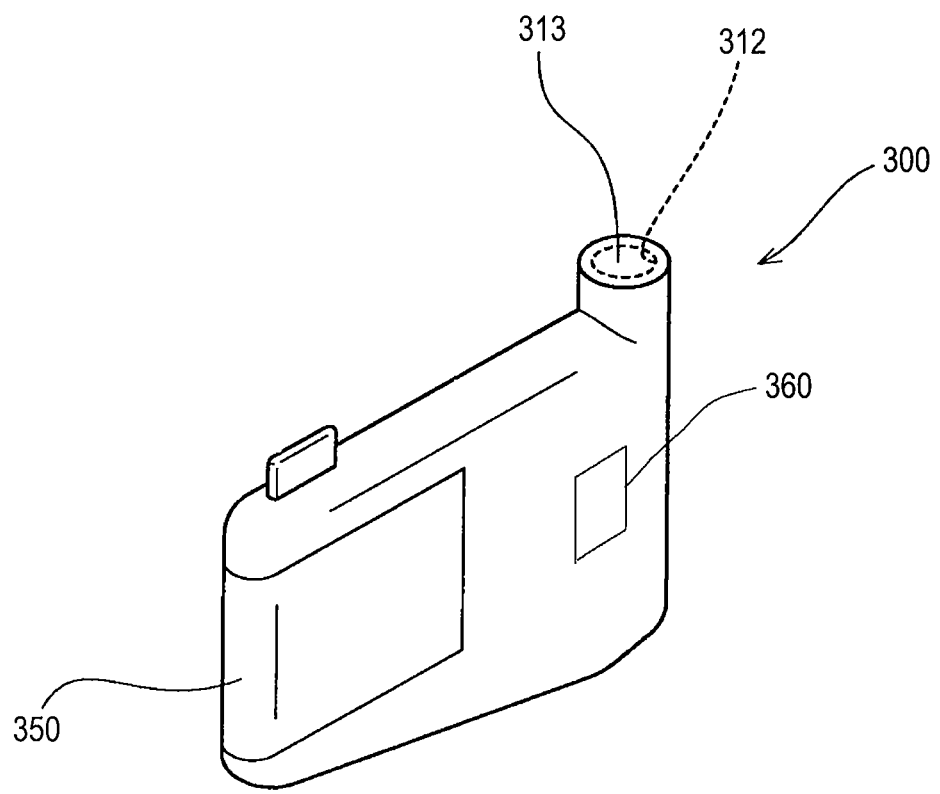
FIG. 10 is a perspective view showing the configuration of the reagent container according to the embodiment.

FIGS. 9 and 10 are perspective views each showing the configuration of a reagent container according to this embodiment. In this embodiment, as shown in FIGS. 9 and 10, the reagent containers 200 having a large size (capacity about 100 mL) and the reagent containers 300 having a small size (capacity about 20 mL) are used in accordance with the kind of reagent to be contained. That is, the reagent containers 200 having a large size contain a staining liquid for sub-class classification of white blood cells and the reagent containers 300 having a small size contain a staining liquid for detection of reticulocyte and a staining liquid for detection of platelets. The reagent containers 200 and 300 have the opening sections 212 and 312, into which the piercer 64 is inserted, at the upper portion of the front end (end in the insertion direction when being inserted into the reagent container installation section 62), and the front portions in which the opening sections 212 and 312 are provided, respectively, have the same shape. In addition, the rear portion (opposite portion to the front side at which the opening section 212 is provided) of the reagent container 200 having a large size have a large width. The reagent container 300 having a small size is formed to have a uniform width over the entire length. In this manner, since the front portions of the reagent containers 200 and 300 have a common shape, the reagent containers can be set in the reagent container installation sections 62 of the holder sections 660a to 660e having the same shape, respectively. Further, as shown in FIGS. 9 and 10, the RFID tags 260 and 360 are respectively attached to the corresponding portions in the side surfaces of the front portions of both of the reagent container 200 having a large size and the reagent container 300 having a small size. The front portions of the reagent containers 200 and 300 have the same shape. Accordingly, in a state in which the reagent containers 200 and 300 are installed in the reagent container installation section 62, the RFID tags 260 and 360 provided in any of the reagent containers 200 and 300 are disposed at positions next to the corresponding antennas 62a to 62e, respectively.

As shown in FIGS. 9 and 10, the opening section 212 (312) is formed in a cylindrical shape protruding upward from the front portions of the reagent containers 200 and 300. The protruding opening sections 212 (312) is provided with a sealing material 213 (313) made of aluminum foil to seal the reagent container 200 (300). As described above, when the cover 663 is closed and the piercer 64 is lowered in conjunction with the closure in a state in which the reagent containers 200 and 300 are installed in the reagent container installation section 62, the sealing materials 213 and 313 are punctured by the tip end of the piercer 64 and the piercer 64 is inserted into the opening sections 212 and 312.

In addition, as shown in FIGS. 9 and 10, the label 250 (350), on which the name of the reagent contained, the lot number of the reagent, the expiration date and the like are printed, is adhered to each reagent container 200 (300). This label 250 (350) is adhered over the rear side surface and at least one of the lateral side surfaces of each reagent container 200 (300). In addition, the label 250 (350) is partially (portion corresponding to the rear side surface of each reagent container 200 (300)) or entirely colored with a color indicating the kind of the reagent contained and thus the kind of the reagent can be identified with the color displayed in the label 250 (350). It can be confirmed whether the reagent container 200 (300) is set in the correct one of holder sections 660a to 660e depending on whether the color of this label 250 (350) matches the color of the label 632 (see FIG. 5) adhered to the cover 663 of the reagent container holder 660.

<Configuration of Sample Transport Unit>

As shown in FIGS. 1 and 2, the sample transport unit 4 has a pre-analysis rack holding section 41 which can hold a plurality of racks 101 accommodating sample containers 100 each containing a sample before analysis, a post-analysis rack holding section 42 which can hold a plurality of racks 101 accommodating sample containers 100 each containing a sample after analysis, a rack transport section 43 which horizontally and linearly moves racks 101 in the direction of the arrows X1 and X2, a barcode reading section 44, a presence detection sensor 45 which detects the presence or absence of a sample container 100 and a rack output section 46 which moves racks 101 in the post-analysis rack holding section 42.

The pre-analysis rack holding section 41 has a rack input section 411 and is configured to push the racks 101 held in the pre-analysis rack holding section 41 onto the rack transport section 43 one by one due to the movement of the rack input section 411 in the direction of the arrow Y2.

As shown in FIG. 2, the rack transport section 43 is configured so that due to the transport of a rack 101, predetermined sample containers 100 held in the rack are arranged at an intake position 43a at which the first measuring unit 3 takes a sample and the intake position 43b at which the second measuring unit 2 takes a sample. In addition, the rack transport section 43 is configured to transport sample containers 100 to a sample detection position 43c at which the presence detection sensor 45 confirms the presence or absence of a sample container 100 and a reading position 43d at which the barcode reading section 44 reads the barcode (not shown) (see FIG. 4) of a sample container 100.

The rack output section 46 is disposed to be opposed to the post-analysis rack holding section 42 with the rack transport section 43 interposed therebetween and is configured to horizontally move in the direction of the arrow Y1. In addition, the rack output section 46 is configured to push a rack 101 disposed at a position between the rack output section 46 and the post-analysis rack holding section 42 of the rack transport section 43 to the post-analysis rack holding section 42 due to the horizontal movement in the direction of the arrow Y1.

<Configuration of Information Processing Unit>

Figure 11:
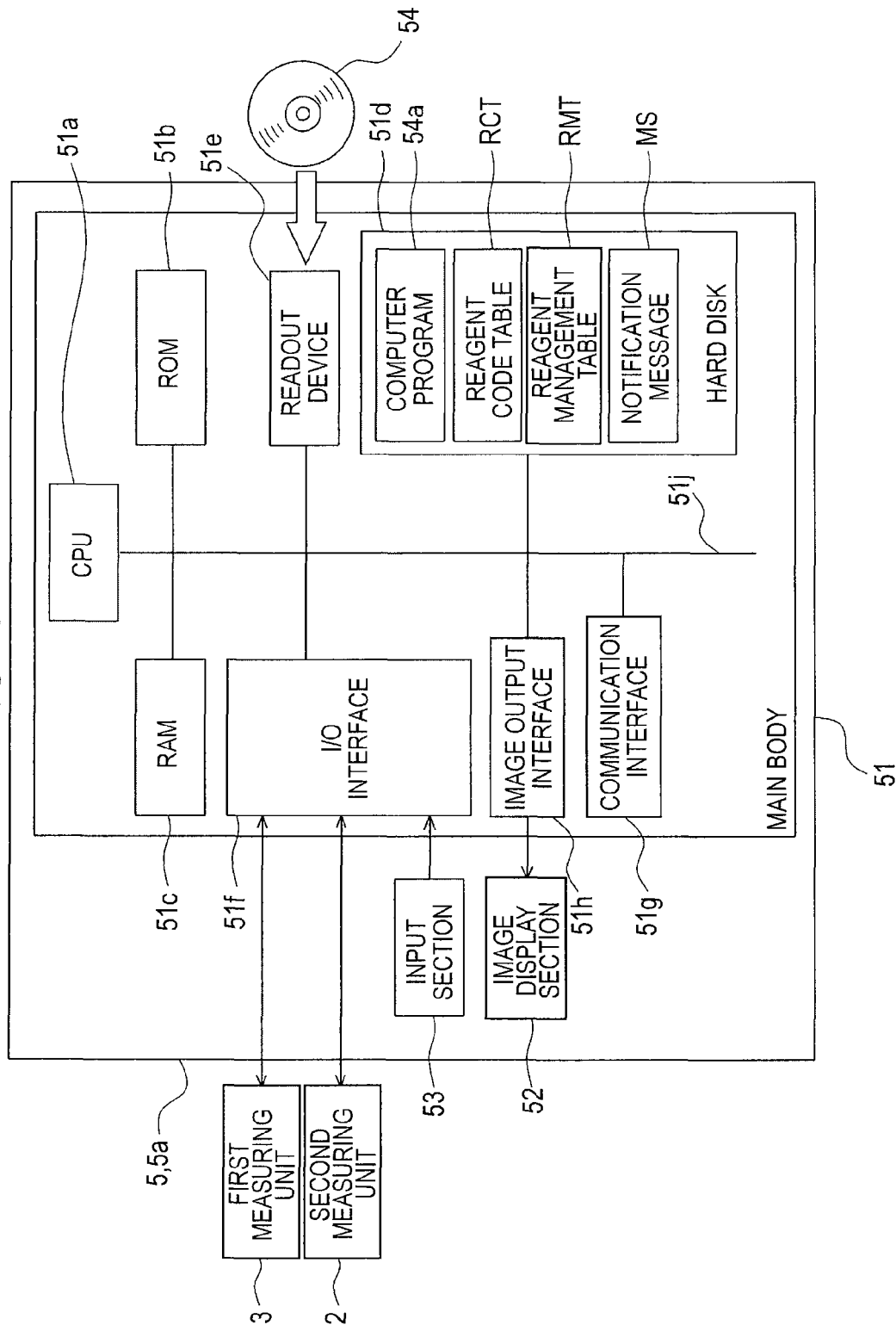
FIG. 11 is a block diagram showing the configuration of an information processing unit according to the embodiment.

Next, the configuration of the information processing unit 5 will be described. The information processing unit 5 is composed of a computer. FIG. 11 is a block diagram showing the configuration of the information processing unit 5. The information processing unit 5 is realized by a computer 5a. As shown in FIG. 11, the computer 5a includes a main body 51, an image display section 52 and an input section 53. The main body 51 includes a CPU 51a, a ROM 51b, a RAM 51c, a hard disk 51d, a readout device 51e, an I/O interface 51f, a communication interface 51g and an image output interface 51h. The CPU 51a, the ROM 51b, the RAM 51c, the hard disk 51d, the readout device 51e, the I/O interface 51f, the communication interface 51g and the image output interface 51h are connected to each other by a bus 51j.

The readout device 51e reads out from a portable recording medium 54 a computer program 54a for prompting the computer to function as the information processing unit 5 and can install the computer program 54a on the hard disk 51d.

Figure 12:
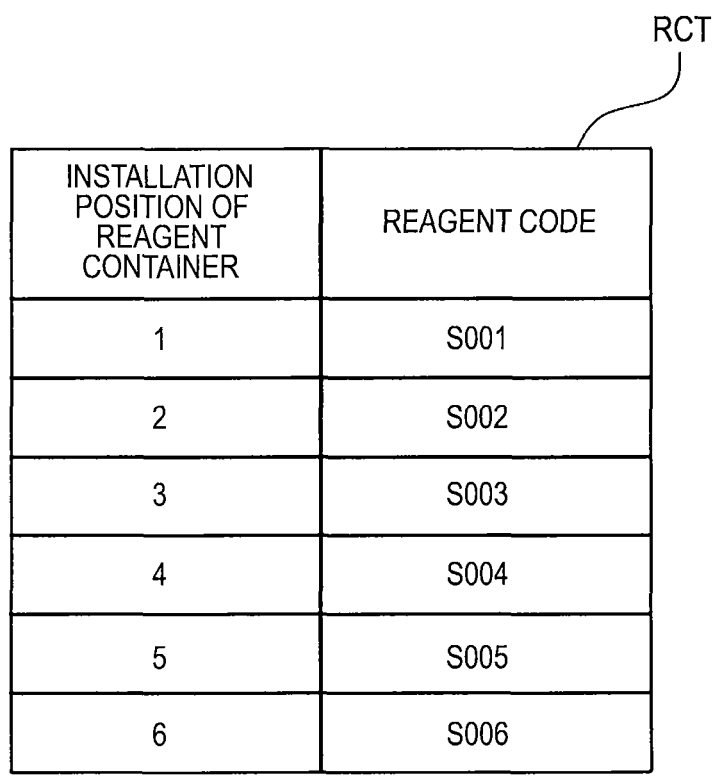
FIG. 12 is a schematic view showing the structure of a reagent code table according to the embodiment.

In the hard disk 51d, a reagent code table RCT is stored in which information specifying the holder sections 660a to 660e and reagent codes indicating the kinds of the reagents which can be installed in the holder sections 660a to 660e are stored in association with each other. FIG. 12 is a schematic view showing the structure of the reagent code table. As described above, for each of the holder sections 660a to 660e, the kind of the reagent which can be installed is decided. That is, in the holder section 660a, a reagent container is installed containing a staining liquid for first sub-class classification of white blood cells, in the holder section 660b, a reagent container is installed containing a staining liquid for second sub-class classification of white blood cells, in the holder section 660c, a reagent container is installed containing a staining liquid for third sub-class classification of white blood cells, in the holder section 660d, a reagent container is installed containing a staining liquid for detection of reticulocyte, and in the holder section 660e, a reagent container is installed containing a staining liquid for detection of platelets. In the reagent code table RCT, a reagent code "S001" of the staining liquid for first sub-class classification of white blood cells is stored in association with a reagent installation position number "1" indicating the holder section 660a, a reagent code "S002" of the staining liquid for second sub-class classification of white blood cells is stored in association with a reagent installation position number "2" indicating the holder section 660b, a reagent code "S003" of the staining liquid for third sub-class classification of white blood cells is stored in association with a reagent installation position number "3" indicating the holder section 660c, a reagent code "S004" of the staining liquid for detection of reticulocyte is stored in association with a reagent installation position number "4" indicating the holder section 660d, and a reagent code "S005" of the staining liquid for detection of platelets is stored in association with a reagent installation position number "5" indicating the holder section 660e.

In addition, in the hard disk 51d, an area of a reagent management table RMT is provided. The reagent management table RMT is a table for managing the reagents which are installed in the reagent container holder 660 and stores information such as an installation position (holder section) of the reagent, a reagent code, an expiration date of the reagent, the maximum number of uses of the reagent, a serial number, a lot number, an expiry date after opening, and opening date and the number of uses.

Further, in the hard disk 51d, notification messages MS are stored. The notification messages MS are text information which is output when the reagent replacement is needed or a user replaces the reagent. In greater detail, in the hard disk 51d, various notification messages MS are stored such as "There is no reagent. Please open the cover and replace the reagent container.", "A cover not corresponding to the replacement target has been opened. Please close the cover.", "Please set an appropriate reagent container.", "The appropriate reagent container has been set. Please close the cover." and "The reagent replacement has been completed."

Each of the first measuring unit 3 and the second measuring unit 2 are connected to the I/O interface 51f via a cable. The I/O interface 51f is connected to the driver substrates 3a and 2a of the first measuring unit 3 and the second measuring unit 2 so as to communicate therewith and can output a control signal to the driver substrates 3a and 2a. Such driver substrates 3a and 2a receiving the control signal decode this control signal and drive the actuators for the mechanism sections in accordance with the control signal. In addition, the bubble sensor 22p, the five cover opening/closing sensors 63a and the RFID readers 61a to 61e are connected to the driver substrates 3a and 2a, and signals which are output from the bubble sensor 22p, the five cover opening/closing sensors 63a and the RFID readers 61a to 61e are transmitted to the information processing unit 5 via the driver substrates 3a and 2a.

[Operation of Sample Analyzer]

Hereinafter, the operation of the sample analyzer 1 according to this embodiment will be described.

<Sample Analysis Operation>

First, the sample analysis operation of the sample analyzer 1 will be described. The sample analysis is performed when the CPU 51*a* of the information processing unit 5 executes a sample analysis control process and thus controls the first measuring unit 3, the second measuring unit 2 and the sample transport unit 4. FIG. 13 is a flowchart showing the procedures of the sample analysis control process of the information processing unit 5.

In the sample analyzer 1 according to this embodiment, in a state in which the sample analyzer 1 is powered off and thus the sample analyzer is not started up, the solenoid 668 is not supplied with a current and the locking of the respective covers 663 is released. Accordingly, in a state in which the sample analyzer is in the power-off state, a user can freely open and close the cover 663 and replace the reagent.

When power is applied to the sample analyzer 1 and thus the sample analyzer 1 is started up, the CPU 51*a* starts the supply of a current to the respective solenoids 668 and locks the respective covers 663 in the closed position (Step S101). In that state, the CPU 51*a* performs an initialization operation including control of the first measuring unit 3, the second measuring unit 2 and the sample transport unit 4 and a check of the operations of the mechanisms (Step S102). Accordingly, a user is prohibited from opening the cover 663 during the initialization operation, and occurrence of abnormality in the operation of the sample analyzer 1 due to the removal of a reagent container or the replacement by an inappropriate reagent container during the operation of the first measuring unit 3 or the second measuring unit 2 is prevented.

In addition, in this initialization operation, the CPU 51*a* drives the RFID readers 61*a* to 61*e*, reads reagent information from the RFID tags 360 and 260 of the reagent containers 300 and 200 which are installed in the respective reagent container holders 660 of the first measuring unit 3 and the second measuring unit 2, compares reagent codes included in the reagent information with reagent codes stored in the reagent code table, and determines whether the appropriate reagent is installed. In addition, in this process, it is also determined whether the remaining reagent runs out, whether the expiration date of the reagent has expired and whether the expiry date after opening which is decided by an opening date of the reagent has expired, and on the basis of the determination, it is determined whether the reagent installed is appropriate. In this process, when the reagent is not appropriate, the CPU 51*a* executes the same process as a reagent replacement control process to be described later. However, since the sample measurement is not performed during the initialization operation, a measurement stop process of Step S202 is not executed.

When the initialization operation is completed, the sample analyzer 1 enters a standby state to start the sample measurement. Here, the CPU 51*a* stops the supply of a current to the respective solenoids 668 and releases the locking of the covers 663 (Step S103). Accordingly, in the standby state, the cover 663 can be opened and closed and a user can perform reagent replacement.

When starting the sample analysis using the sample analyzer 1, a user operates the information processing unit 5 to give a sample analysis start instruction to the sample analyzer 1. The CPU 51*a* awaits the reception of such a sample analysis start instruction (NO in Step S104), and when receiving the sample analysis start instruction (YES in Step S104), re-starts the supply of a current to the respective solenoids 668 and locks the respective covers 663 in the closed position (Step S105). Accordingly, a user is prohibited from opening the cover 663 during the sample measurement, and occurrence of abnormality in the operation of the sample analyzer 1 due to the removal of a reagent container or the replacement by an inappropriate reagent container during the operation of the first measuring unit 3 or the second measuring unit 2 is prevented.

The CPU 51*a* prompts the sample transport unit 4 to transport the rack 101 (Step S106), prompts the barcode reading section 25*c* to read the barcode adhered to a first sample container 100 (on the furthest downstream side in the transport direction in the rack 101), and obtains sample information (sample ID, measurement order, patient information and the like) of the sample (Step S107). From this sample information, the CPU 51*a* decides the measuring unit for performing the measurement of the sample from between the first measuring unit 3 and the second measuring unit 2 (Step S108), takes the sample container 100 into the decided measuring unit and suctions the sample from the sample container 100 to the sample suction section 21 or 31 (Step S109). The sample container 100 in which the suctioning of the sample has been completed is discharged from the measuring unit and is returned to the original position in the rack 101.

After the suctioning of the sample, the CPU 51*a* mixes the sample and a reagent according to the measurement item of the sample and prepares a measurement specimen in the specimen preparation section 22 (Step S110). In this manner, when the measurement specimen is prepared by using the reagent once, the CPU 51*a* updates the number uses of the reagent to the value increased by one in the reagent management table RMT. Further, the CPU 51*a* prompts the specimen preparation section 22 to supply the measurement specimen to the detecting section 23 and prompts the detecting section 23 to measure the sample (Step S111). The CPU 51*a* obtains the measurement data of the sample, analyzes this measurement data and obtains the analysis result of the sample (Step S112). Next, the CPU 51*a* determines whether all the sample containers 100 held in the rack 101 have been supplied to the measuring unit (Step S113). When there is a sample container 100 which is not yet supplied to the measuring unit (NO in Step S113), the CPU returns the process to Step S106, transports the rack 101 and prompts the barcode reading section 25*c* to read the barcode adhered to the subsequent sample container 100 to obtain sample information of the sample. After that, the processes after Step S108 are executed to analyze the sample.

In Step S113, when all the sample containers 100 are supplied to the measuring unit (YES in Step S113), the CPU 51*a* prompts the sample transport unit 4 to transport the rack 101 up to the post-analysis rack holding section 42 (Step S114) and determines whether there is a subsequent rack 101 accommodating sample containers 100 on which the measurement has not yet been performed (Step S115). When there is a subsequent rack 101 (YES in Step S115), the CPU 51*a* returns the process to Step S106 and executes the processes after Step S106 on the samples which are held in the subsequent rack 101. Accordingly, a plurality of the racks 101 is continuously transported and the samples which are held in these racks 101 are sequentially analyzed. When there is no subsequent rack 101 accommodating sample containers 100 on which the measurement has not yet been performed (NO in Step S115), the CPU 51*a* returns the process to Step S103 and releases the locking of the respective covers 663.

In addition, here, the automatic sample analysis operation in which the rack 101 is transported by the sample transport unit 4 has been described, but in the sample analyzer 1, a manual sample analysis operation may also be executed in which a user sets the sample containers 100 one by one without using the sample transport unit 4 and takes the set sample containers 100 into the measuring unit to analyzes the samples.

<Reagent Replacement Operation>

Figure 14A:
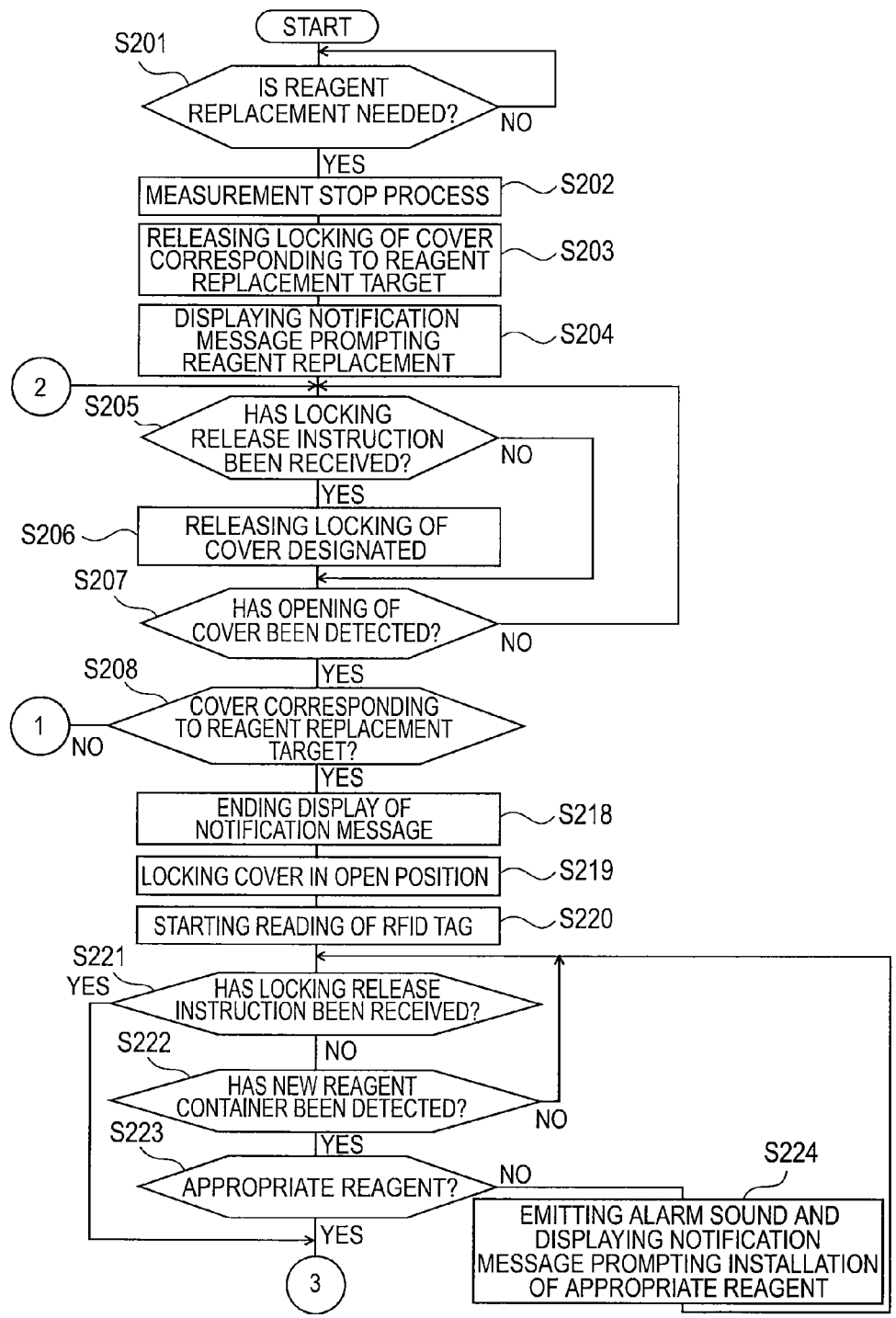
FIG. 14A is a flowchart showing the procedures of a reagent replacement control process of the information processing unit according to the embodiment.
Figure 14B:
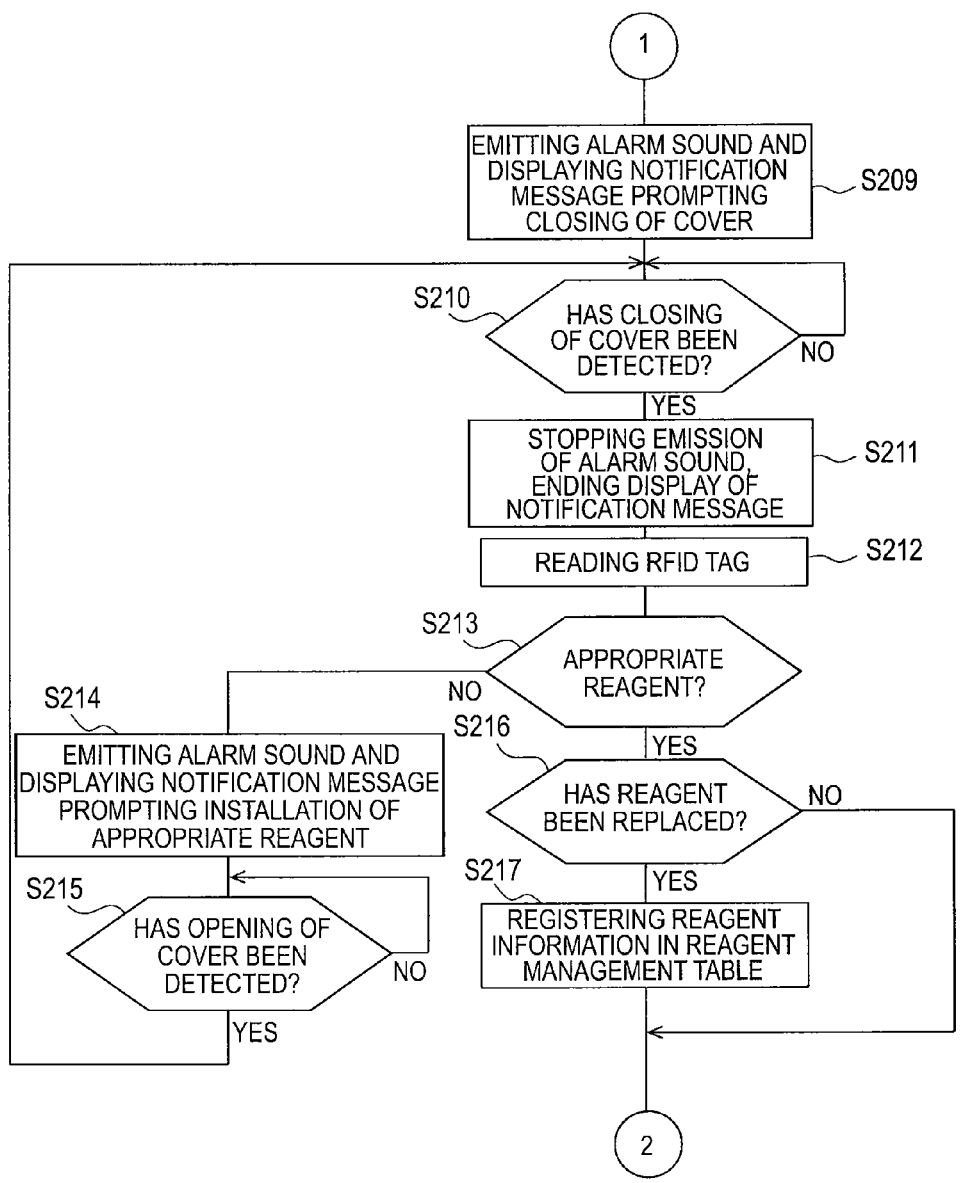
FIG. 14B is a flowchart showing the procedures of the reagent replacement control process of the information processing unit according to the embodiment.
Figure 14C:
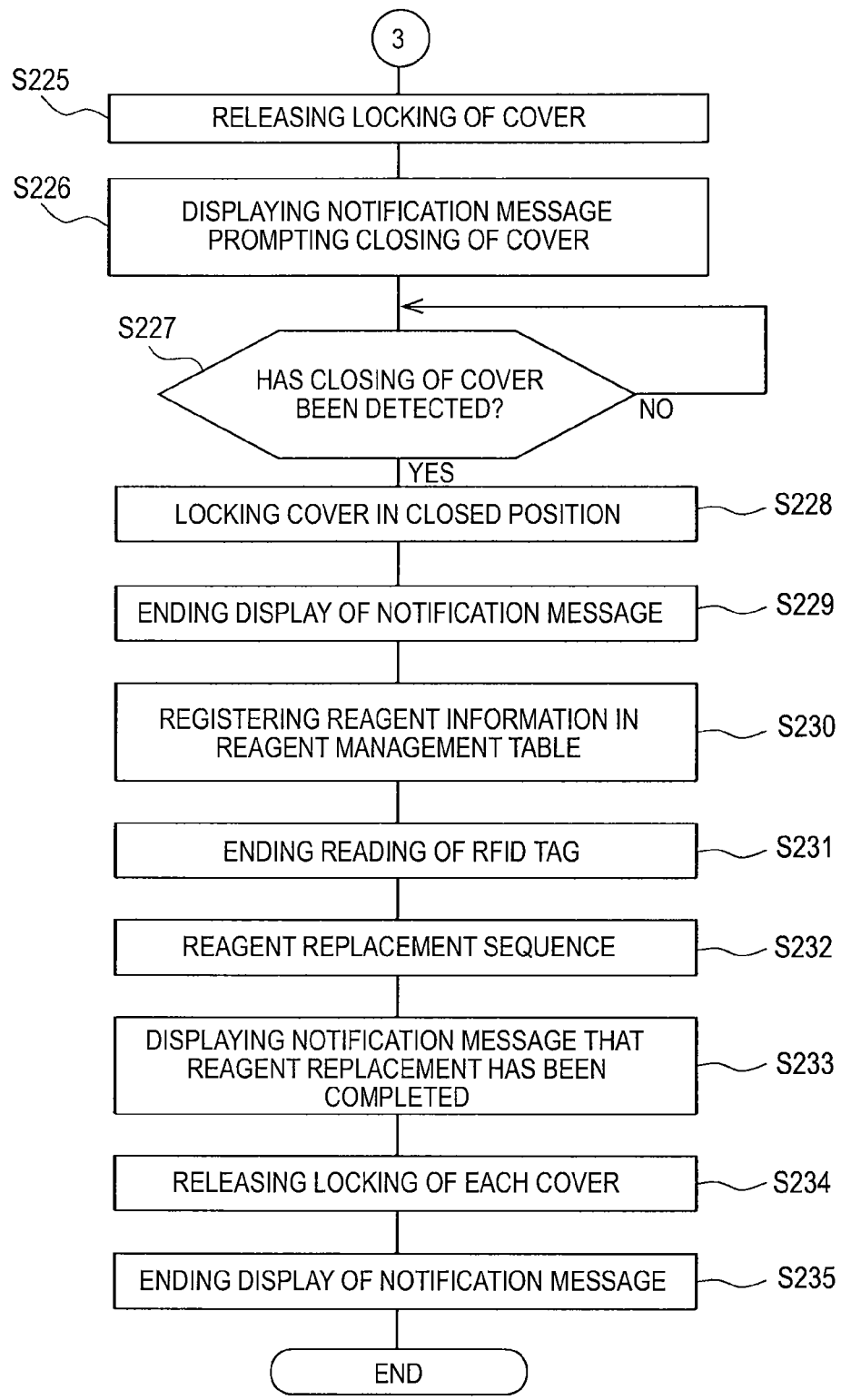
FIG. 14C is a flowchart showing the procedures of the reagent replacement control process of the information processing unit according to the embodiment.

When the reagent is consumed as a result of the above-described sample analysis or when the expiration date of the reagent has been expired, it is necessary to replace the reagent. In the sample analyzer 1 according to this embodiment, the CPU 51a of the information processing unit 5 executes a reagent replacement control process to control the first measuring unit 3 or the second measuring unit 2, and thus a reagent replacement operation is performed. FIGS. 14A to 14C are flowcharts showing the procedures of the reagent replacement control process of the information processing unit 5 according to this embodiment. First, the CPU 51a determines whether the reagent replacement is needed (Step S201). In this process, when the reagent is consumed due to the analysis and the number of uses the reagent matches the maximum number of uses in the reagent management table RMT, that is, when the remaining reagent runs out, the reagent replacement is determined to be needed. In addition, also in the case in which the bubble sensor 22p detects bubbles in the reagent which is supplied to the reaction chamber 22a from the reagent container 200 or 300, it is determined that the remaining reagent runs out and the reagent replacement is needed. Further, also in the case in which the expiration date of the reagent has expired or the case in which the expiry date after opening which is decided by an opening date of the reagent has expired, the reagent replacement is determined to be needed.

When the reagent replacement is not needed in Step S201 (NO in Step S201), the CPU 51a repeats the process of Step S201 until the reagent replacement is needed. On the other hand, when the reagent replacement is determined to be needed (YES in Step S201), the CPU 51a executes a measurement stop process of the first measuring unit 3 or the second measuring unit 2 (Step S202). When the automatic sample analysis operation is executed, this measurement stop process is a process of controlling the first measuring unit 3 or the second measuring unit 2 so that the measurement of a sample on which the measurement has not yet been performed does not start and a sample during the measurement at that time is measured until the end. When the manual sample analysis operation is executed, this measurement stop process is a process of controlling the first measuring unit 3 or the second measuring unit 2 so that a sample during the measurement at that time is measured until the end and a new sample is not received.

When the measurement stop process ends, the CPU 51a stops the supply of a current to the solenoid 668 corresponding to the reagent replacement target holder section and releases the locking of the cover 663 of the holder section corresponding to the reagent replacement target (Step S203). Accordingly, the cover 663 can be opened and closed.

Next, the CPU 51a reads out a notification message MS from the hard disk 51d and displays the notification message "There is no reagent. Please open the cover and replace the reagent container." on the image display section 52 (Step S204). In addition, in Step S204, the CPU 51a emits an alarm sound from the buzzer 29 or 39 in accordance with the above-described notification message.

In Step S204, in accordance with the above-described notification message, the image display section 52 displays the name of the reagent which should be replaced and information which shows the measuring unit requiring the replacement of the reagent. The information to be displayed which shows the measuring unit requiring the replacement of the reagent may be, for example, letter information such as a name of the first measuring unit 3 or the second measuring unit 2, a unit number, "right measuring unit" or "left measuring unit". Otherwise, image information may be used in which pictures of the first measuring unit 3 and the second measuring unit 2 are displayed and the measuring unit requiring the reagent replacement is displayed with a color different from that of the measuring unit not requiring the reagent replacement. Both of the text information and the image information may be combined.

By such a notification message, a user knows the kind of the reagent which should be replaced and the measuring unit requiring the reagent replacement in addition to the information that the reagent replacement is needed. The user prepares a new reagent for replacement and opens the front cover 24a or 34a of the measuring unit requiring the reagent replacement. The user checks the labels 632 adhered to the respective covers 663 of the regent container holder 660, specifies the holder section corresponding to the reagent replacement target among the holder sections 660a to 660e and opens the cover 663 of the holder section corresponding to the reagent replacement target. In this manner, when the cover 663 is opened, the cover opening/closing sensor 63a corresponding to the cover 663 detects the opening of the cover 663 and outputs a detection signal.

In addition, here, the user may want to replace a reagent other than the reagent which is a replacement target because the amount remaining of the reagent is small or the expiration date is close. In such a case, the user presses the pressing button switch 667 corresponding to the reagent container installation section 62 in which a reagent container to be replaced is installed to give a locking release instruction of the cover 663 corresponding to the reagent container installation section 62 to the sample analyzer 1. The CPU 51a monitors a detection signal of the pressing button switch 667 and determines whether the locking release instruction has been received (Step S205). When the locking release instruction has been received (YES in Step S205), the supply of a current to the solenoid 668 corresponding to the pressed pressing button switch 667 is stopped and the locking of the cover 663 is released (Step S206). Accordingly, the cover 663 not corresponding to the reagent replacement target can be opened and closed. In this manner, when the user opens the cover 663 in which the locking has been released, the cover opening/closing sensor 63a corresponding to the cover 663 detects the opening of the cover 663 and outputs a detection signal.

When the locking of the cover is released in Step S206 or the locking release instruction is not received in Step S205 (NO in Step S205), the CPU 51a determines whether the opening of the cover 663 is detected by the detection signal of the cover opening/closing sensor 63a (Step S207). When the opening of the cover 663 is not detected (NO in Step S207), the CPU 51a returns the process to Step S205 and determines once again whether a locking release instruction has been received.

On the other hand, when the opening of the cover 663 is detected in Step S207 (YES in Step S207), the CPU 51a determines whether the opened cover 663 is a cover of the holder section corresponding to the reagent replacement target (Step S208). When the opened cover 663 is different from the cover of the holder section corresponding to the reagent replacement target (NO in Step S208), the CPU 51a reads a notification message MS from the hard disk 51d, displays the notification message "A cover not corresponding to the replacement target has been opened. Please close the cover." on the image display section 52 and prompts the buzzer 39 or 29 to emit an alarm sound (Step S209). Accordingly, the user is notified of the opening of the cover of the holder section not corresponding to the reagent replacement target and is warned.

When the user closes the opened cover 663, the cover opening/closing sensor 63a corresponding to this cover detects the closing of the cover. The CPU 51a determines whether the cover 663 has been closed by an output signal of the cover opening/closing sensor 63a (Step S210). When the closing of the cover 663 is not detected (NO in Step S210), the CPU 51a repeats the process of Step S210 until the closing of the cover 663 is detected.

On the other hand, when the closing of the cover 663 is detected in Step S210 (YES in Step S210), the CPU 51a prompts the buzzer 39 or 29 to stop emission of the alarm sound and ends the display of the notification message (Step S211). At this time, the notification message that the display is ending is a notification message which is displayed in Step S209 and prompts the closing of the cover, and the display of the notification message which is displayed in Step S204 and prompts the replacement of the reagent is maintained. At this time, the display of this notification message ends when a notification message, which is displayed in Step S214 to be described later, prompting the installation of an appropriate reagent is displayed.

Here, in the holder section of which the cover 663 has been opened once, the reagent container may be replaced. For example, a reagent other than the reagent which is a replacement target may be replaced because the amount remaining of the reagent is small or the expiration date is close. In addition, it is also considered that the user opens the cover 663 of another holder section different from the holder section corresponding to the reagent which is a replacement target and replaces a reagent container therein with a new reagent container which is a replacement target. Accordingly, the CPU 51a drives the RFID reader of the holder section in which the cover 663 is closed, reads reagent information from the RFID tag 260 of the reagent container 200 or the RFID tag 360 of the reagent container 300, either of which is installed in the holder section (Step S212) and determines whether the appropriate reagent is installed (Step S213). In this process, the CPU 51a reads out a reagent code corresponding to the holder section in which the cover 663 is opened from the reagent code table RCT, and through the determination whether the read reagent code matches the reagent code which is included in the reagent information output from the RFID tag 260 or 360, it is determined whether the reagent container installed in the holder section is appropriate.

In Step S213, when the replaced reagent is not appropriate (NO in Step S213), the CPU 51a reads a notification message MS from the hard disk 51d, displays the notification message "Please set an appropriate reagent container." on the image display section 52 and prompts the buzzer 39 or 29 to emit an alarm sound (Step S214). Accordingly, the user is notified of the fact that the inappropriate reagent is installed in the holder section and the installation of an appropriate reagent is prompted. Further, the CPU 51a determines once again whether the opening of the cover 663 is detected by a detection signal of the cover opening/closing sensor 63a (Step S215). When the opening of the cover 663 is not detected (NO in Step S215), the CPU 51a repeats the process of Step S215 until the opening of the cover 663 is detected.

On the other hand, when the opening of the cover 663 is detected in Step S215 (YES in Step S215), the CPU 51a returns the process to Step S210 and determines whether the cover 663 is closed.

In Step S213, when the appropriate reagent is installed in the holder section in which the cover 663 is closed, that is, when the reagent code of the reagent installed in the holder section matches the reagent code associated with the holder section (YES in Step S213), the CPU 51a determines whether the reagent has been replaced in the holder section (Step S216). In the reagent management table RMT, information related to the reagents installed is registered and unique serial numbers of the reagents are included. That is, when the serial number read from the RFID tag 260 or 360 matches the serial number of the reagent at the installation position, which is registered in the reagent management table RMT, it can be determined that the reagent installed in the holder section before the opening and closing of the cover 663 is the same as the reagent installed in the holder section after the opening and closing of the cover 663 and the reagent has not been replaced. On the other hand, when the serial number read from the RFID tag 260 or 360 does not match the serial number of the reagent at the installation position, which is registered in the reagent management table RMT, it can be determined that the reagent installed in the holder section before the opening and closing of the cover 663 is different from the reagent installed in the holder section after the opening and closing of the cover 663 and the reagent has been replaced. In the process of Step S216, the CPU 51a matches the serial number of the reagent read out from the RFID tag 260 or 360 to the serial number of the reagent at the installation position, which is registered in the reagent management table RMT, to determine whether the reagent has been replaced.

In Step S216, when the reagent has been replaced in the holder section (YES in Step S216), the CPU 51a stores the reagent information read out from the RFID tag 360 or 260 in association with the installation position indicating the holder section in the reagent management table RMT (Step S217). In this case, the reagent information corresponding to the installation position which has been stored in the reagent management table RMT, that is, the reagent information related to the reagent before the replacement is deleted. The CPU 51a executes the process of Step S217 and then returns the process to Step S205. On the other hand, in Step S216, when the reagent has not been replace in the holder section (NO in Step S216), the CPU 51a returns the process to Step S205.

In Step S208, when the opened cover 663 is a cover of the holder section corresponding to the reagent replacement target (YES in Step S208), the CPU 51a ends the display of the notification message prompting the replacement of the reagent, which is displayed in Step S204 (Step S218).

In Step S218, when the display of the notification message prompting the replacement of the reagent ends, the CPU 51a supplies a current to the solenoid 668 corresponding to the opened cover 663 and locks the cover 663 in the open position (Step S219). Accordingly, in the case in which the reagent is not replaced, and in the case in which the appropriate reagent is not installed, the closing of the cover 663 is prevented and the reagent replacement is appropriately and reliably performed.

Next, the CPU 51a drives the RFID reader of the holder section in which the cover 663 is opened and starts the reading of the reagent information from the RFID tag 260 of the reagent container 200 or the RFID tag 360 of the reagent container 300, either of which is installed in the holder section (Step S220). In this process, the RFID reader is driven and transmission of the electric wave from the antenna connected to this RFID reader is started. Here, when the reagent container 300 or 200 is replaced in the holder section, the RFID reader reads out reagent information from the RFID tag 360 adhered to a new reagent container 300 or the RFID tag 260 adhered to a new reagent container 200.

Meanwhile, the user may not want to replace the reagent, such as when the user has no appropriate reagent. In this case, the user presses the pressing button switch 667 provided in the cover 663 which is locked in the open position and gives a locking release instruction to the sample analyzer 1. The CPU 51*a* determines whether such a locking release instruction has been received (Step S221). When the locking release instruction has been received (YES in Step S221), the CPU proceeds the process to Step S225 and release the locking of the cover 663 (Step S225). Accordingly, when there is no need to replace the reagent or the reagent replacement is not performed, the user can close the cover 663 without performing the reagent replacement.

On the other hand, when the locking release instruction has not been received in Step S221 (NO in Step S221), the CPU 51*a* determines whether a new reagent container has been installed on the basis of the reagent information read out as described above (Step S222). In this process, the CPU 51*a* matches the serial number of the reagent read out from the RFID tag 260 or 360 to the serial number of the reagent at the installation position, which is registered in the reagent management table RMT. When both of them match, the CPU determines that a new reagent container has not been installed, and when both of them do not match, the CPU determines that a new reagent container has been installed. When the installation of a new reagent container is not detected in Step S222 (NO in Step S222), the CPU 51*a* repeats the process of Step S222 until the installation of a new reagent container is detected.

On the other hand, in Step S222, when the installation of a new reagent container is detected (YES in Step S222), the CPU 51*a* determines whether the replaced reagent is appropriate (Step S223). Since the process of Step S223 is the same as the process of Step S213, the description thereof will be omitted.

In Step S223, when the replaced reagent is not appropriate (NO in Step S223), the CPU 51*a* reads out a notification message MS from the hard disk 51*d*, displays the notification message "Please set an appropriate reagent container." on the image display section 52, prompts the buzzer 39 or 29 to emit an alarm sound (Step S224) and returns the process to Step S221. Accordingly, the user is notified of the fact that the inappropriate reagent is installed in the holder section and the installation of an appropriate reagent is prompted.

On the other hand, in Step S223, when the replaced reagent is appropriate (YES in Step S223), the CPU 51*a* stops the supply of a current to the solenoid 668 corresponding to the cover 663 which is in the open position and release the locking of the cover 663 (Step S225). Accordingly, the cover 663 can be closed after the installation of the appropriate reagent.

Next, the CPU 51*a* reads out a notification message MS from the hard disk 51*d* and displays the notification message "The appropriate reagent container has been set. Please close the cover." on the image display section 52 (Step S226). In this case, when another notification message is displayed on the image display section with the emission of the alarm sound, the CPU 51*a* ends the display of the other notification message and stops the emission of the alarm sound.

Next, the CPU 51*a* determines whether the cover 663 is closed by an output signal of the cover opening/closing sensor 63*a* (Step S227). When the closing of the cover 663 is not detected (NO in Step S227), the CPU 51*a* repeats the process of Step S227 until the closing of the cover 663 is detected.

On the other hand, when the closing of the cover 663 is detected in Step S227 (YES in Step S227), the CPU 51*a* re-starts the supply of a current to the solenoid 668 corresponding to the cover 663 that closing is detected, and locks the cover 663 in the closed position (Step S228). Accordingly, re-replacement by a wrong reagent is prevented.

Next, the CPU 51*a* ends the display of the notification message prompting the closing of the cover, which is displayed in Step S226 (Step S229), and registers the reagent information read out from the RFID tag 360 or 260 in the reagent management table RMT (Step S230). In this process, the reagent information corresponding to the installation position which has been stored in the reagent management table RMT, that is, the reagent information related to the reagent before the replacement is deleted and the reagent information read out from the RFID tag 360 or 260 is stored in association with the installation position indicating the holder section.

Next, the CPU 51*a* stops the driven RFID reader and ends the readout of the reagent information from the RFID tag 260 of the reagent container 200 or the RFID tag 360 of the reagent container 300, either of which is installed in the holder section provided with the RFID reader (Step S231).

In addition, the CPU 51*a* executes a reagent replacement sequence (Step S232). The reagent replacement sequence is a control process of the first measuring unit 3 or the second measuring unit 2 to suction a predetermined amount of reagent from a reagent container replaced and discard the reagent collected as a result in the reaction chamber 22*a* in order to eliminate bubbles which are generated in the flow passage from the piercer 64 to the reaction chamber 22*a* due to the reagent replacement in the first measuring unit 3 or the second measuring unit 2.

When the reagent replacement sequence ends, the CPU 51*a* reads out a notification message MS from the hard disk 51*d* and displays the notification message "The reagent replacement has been completed." on the image display section 52 (Step S233).

After the display of the notification message that the reagent replacement has been completed on the image display section 52 in Step S233, the CPU 51*a* stops the supply of a current to the respective solenoids 668 and releases the locking of the respective covers 663 (Step S234). After elapse of a predetermined time from the display of the notification message in Step S233, the CPU 51*a* ends the display of the notification message (Step S235) and ends the reagent replacement control process.

Due to the above-described configuration, in the sample analyzer 1 according to this embodiment, the solenoid 668 is provided locking the cover 663 in the open position and releasing the locking, and the CPU 51*a* of the information processing unit 5 controls the locking of the cover 663 in the open position by this solenoid and the release thereof. Accordingly, when the reagent is replaced, it is possible to prevent the closing of the cover 663 at the time when the cover 663 which is in the open position should not be closed. For example, in this embodiment, when the cover 663 is opened when performing the reagent replacement, the cover 663 is locked in this open position, and thus even when the replacement is performed with a reagent container containing an inappropriate reagent, it is possible to easily perform the re-replacement by an appropriate reagent without the closing of the cover 663.

In addition, in the sample analyzer 1 according to this embodiment, the cover opening/closing sensor 63*a* can individually detect the opening of the covers 663. Accordingly, it is possible to reliably detect that the cover 663 is in an open state and it is possible to reliably lock the cover 663 in the open position.

In addition, the sample analyzer 1 according to this embodiment has a configuration in which the CPU 51*a* determines whether the reagent replacement is needed and locks the opened cover 663 when the reagent replacement is determined to be needed. Accordingly, it is possible to lock the cover in the open position in order to perform the reagent replacement when the reagent replacement is needed, and thus it is possible to smoothly perform the reagent replacement.

In addition, when a new reagent container is installed in the reagent container installation section 62, the reagent code of the reagent is matched to the reagent code of a reagent which should be installed in the reagent container installation section 62 in the reagent code table RCT, and when the installed reagent container is not a reagent container containing a reagent which should be installed in the reagent container installation section 62, a notification message "Please set an appropriate reagent container." is output which prompts the installation of another reagent container. Accordingly, a user can easily recognize the installation of the inappropriate reagent container and easily recognize that next work to be performed is installation of an appropriate reagent container.

In addition, when the notification message prompting the installation of the appropriate reagent is displayed, the cover 663 of the reagent container installation section 62 is locked in the open position and thus it does not occur that the sample measurement operation is executed with the cover 663 closed. In addition, since the cover 663 is locked in the open position until the appropriate reagent is installed, a user can easily perform the re-replacement by an appropriate reagent.

In addition, in the sample analyzer 1 according to this embodiment, the cover 663 can be locked in two positions which are the open position and the closed position. Accordingly, when the reagent replacement is not to be performed, the cover 663 can be locked in the close position, and when the reagent replacement is to be performed, the cover 663 can be locked in the open position, and thus a user can smoothly and reliably perform the reagent replacement.

In addition, the sample analyzer 1 according to this embodiment has a configuration in which when the pressing button switch 667 is pressed and a locking release instruction is received when the cover 663 is locked in the open position, the locking of the cover 663 is released. Accordingly, even if the cover 663 is opened when the reagent replacement is not needed or the reagent replacement cannot be performed because there is no appropriate reagent, a user can easily close the cover 663.

Other Embodiments

In the above-described embodiment, the configuration has been described in which the reagent replacement operation is executed when the sample analyzer determines that the replacement of the reagent is needed, but the invention is not limited thereto. A configuration may be provided in which the reagent replacement operation is executed when the sample analyzer receives a reagent replacement instruction from a user.

Figure 15:
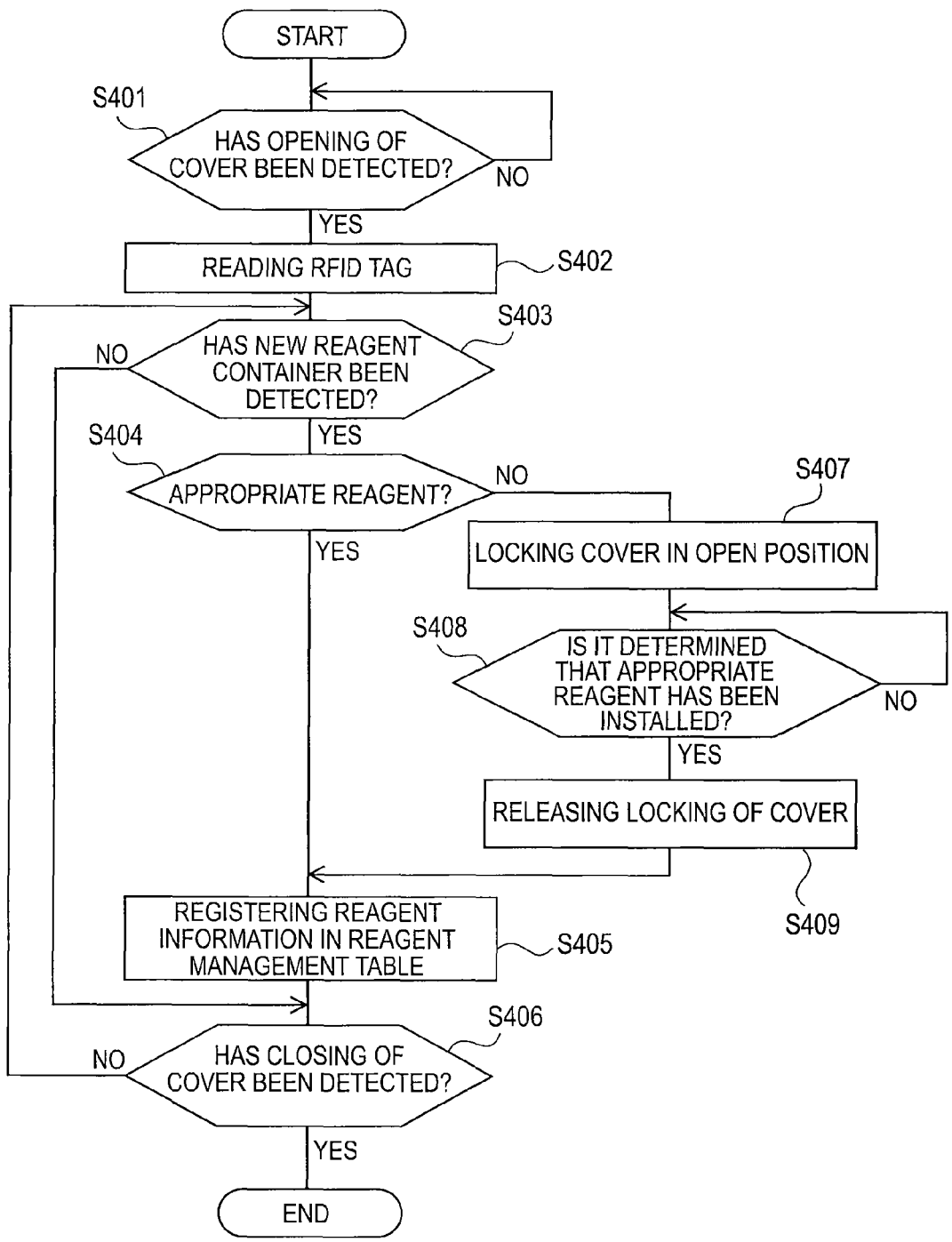
FIG. 15 is a flowchart showing the procedures of a reagent replacement control process of an information processing unit according to another embodiment.

FIG. 15 is a flowchart showing the procedures of a reagent replacement control process for this case. As shown in FIG. 15, when the sample analyzer receives a reagent replacement instruction from a user, the CPU 51*a* determines whether the opening of any of the covers 663 is detected by a detection signal of the cover opening/closing sensor 63*a* (Step S401). When the opening of any of the covers 663 is not detected (NO in Step S401), the CPU 51*a* repeats the process of Step S401 until the opening of any of the covers 663 is detected.

On the other hand, when the opening of any of the covers 663 is detected in Step S401 (YES in Step S401), the CPU 51*a* drives the RFID reader of the holder section in which the cover 663 has been opened, reads out reagent information from the RFID tag 260 of the reagent container 200 or the RFID tag 360 of the reagent container 300, either of which is installed in the holder section (Step S402), and determines whether a new reagent container has been installed (Step S403). The readout of reagent information by the RFID reader is continuously executed until the reagent replacement control process shown in FIG. 15 ends. When it is determined that a new reagent container has been installed in Step S403 (YES in Step S403), the CPU 51*a* determines whether the appropriate reagent is installed in the holder section on the basis of the reagent information continuously read out (Step S404). When the reagent is appropriate (YES in Step S404), the CPU 51*a* stores the reagent information read out from the RFID tag 360 or 260 in association with an installation position indicating the holder section in the reagent management table RMT (Step S405).

Next, the CPU 51*a* determines whether the opened cover 663 has been closed by a detection signal of the cover opening/closing sensor 63*a* (Step S406). When the cover has been closed (YES in Step S406), the CPU ends the process, and when the cover has not been closed (NO in Step S406), CPU returns the process to Step S403.

When determining that a new reagent container has not been installed in Step S403 (NO in Step S403), the CPU 51*a* proceeds the process to Step S406. In addition, when determining that the reagent is not appropriate in Step S404 (NO in Step S404), the CPU 51*a* supplies a current to the solenoid 668 corresponding to the opened cover 663 and locks the cover 663 in the open position (Step S407).

Next, the CPU 51*a* determines whether an appropriate reagent has been installed in the holder section on the basis of the reagent information continuously read out (Step S408). When an appropriate reagent has been installed, the CPU releases the locking of the cover 663 in the open position (Step S409) and the process proceeds to Step S405. On the other hand, when an appropriate reagent has not been installed (NO in Step S408), the CPU 51*a* repeats the process of Step S408 until the appropriate reagent is installed.

In addition, in the above-described embodiment, the configuration has been described in which it is determined whether the appropriate reagent has been installed in Steps S213 and S223, but the invention is not limited thereto. A configuration may be provided in which these steps are omitted and determination whether the appropriate reagent container has been installed is not executed.

In addition, in the above-described embodiment, the configuration has been described in which the cover 663 is locked by inserting the plunger 668*a* of the solenoid 668 into the first locking hole 666*a* and the second locking hole 666*b*, but the invention is not limited thereto. A structure may be employed in which the cover 663 can be locked in the open position and in the closed position, and for example, in order to lock the cover 663, in place of the solenoid, an actuator such as a motor or an air cylinder may engage the locking pin with the locking hole.

In addition, in the above-described embodiment, the configuration has been described in which the single solenoid 668 locks the cover 663 in the open position and in the closed position, but the invention is not limited thereto. A configuration may be provided in which an actuator such as the single solenoid locks the cover 663 in the open position and another actuator locks the cover 663 in the closed position.

In addition, in the above-described embodiment, the configuration has been described in which the cover 663 can be locked in the two positions, that is, in the open position and the closed position, but the invention is not limited thereto. A configuration may be provided in which the cover 663 can be locked only in the open position and the locking in the closed position is not performed.

In addition, in the above-described embodiment, the configuration has been described in which the cover 663 and the piercer 64 are connected to each other by the piercer lifting mechanism 665 and the cover 663 and the piercer 64 are integrally lifted and lowered due to the user's operation, but the invention is not limited thereto. A configuration may be provided in which a driving source such as a motor for lifting and lowering the piercer 64 is provided, and when the cover 663 is moved in the vertical direction, the information processing unit 5 controls the driving source to lift and lower the piercer 64 in conjunction with the lifting and lowering of the cover 663. A configuration may also be provided in which the piercer 64 is lifted and lowered independently from the cover 663.

In addition, in the above-described embodiment, the configuration has been described in which the notification is performed by emitting an alarm sound in addition to the notification message in Steps S204, S209, S214 and S224, but the invention is not limited thereto. A configuration may also be provided in which only a notification message is output without the emission of an alarm sound. A configuration may also be provided in which only an alarm sound is output without the output of a notification message.

In addition, in the above-described embodiment, the configuration has been described in which each of the first and second measuring units takes a sample container 100 into the unit and a sample is suctioned from the sample container 100 in the unit, but the invention is not limited thereto. A configuration may be provided in which the first measuring unit directly suctions a sample from a sample container 100 on the sample transport unit. A configuration may also be provided in which the second measuring unit directly suctions a sample from a sample container 100 on the sample transport unit.

In addition, in the above-described embodiment, the configuration has been described in which the opening of the cover 663 is detected when the cover rises even slightly, and the closing of the cover 663 is detected when the cover is completely closed, but the invention is not limited thereto. The opening of the cover 663 may be detected when the cover 663 is completely opened, and the closing of the cover 663 may be detected when the cover 663 lowers even slightly from the complete opening state. In addition, the opening of the cover 663 may be detected when the cover 663 rises up to a predetermined height, and the closing of the cover 663 may be detected when the cover 663 lowers up to the predetermined height.

In addition, in the above-described embodiment, the five covers 663 are individually provided in the five reagent container installation sections 62, respectively. However, a cover common to the plurality of the reagent container installation sections 62 may be provided and this cover may be locked in the open position and in the closed position.

In addition, in the above-described embodiment, the configuration has been described in which the cover 663 can be locked in the open position and in the closed position. However, a configuration may be provided in which the front covers 24a and 34a can be locked in the open position and in the closed position without provision of the cover 663.

In addition, in the above-described embodiment, the configuration has been described in which the sample analyzer includes the two measuring units which are the first measuring unit and the second measuring unit, but the invention is not limited thereto. The sample analyzer may include three or more measuring units and may include a single measuring unit.

In addition, in the above-described embodiment, the configuration has been described in which the information processing unit which is provided independently of the first measuring unit, the second measuring unit and the sample transport unit controls the first measuring unit, the second measuring unit and the sample transport unit, but the invention is not limited thereto. A configuration may be provided in which a control substrate equipped with a CPU, a memory and the like is provided in each of the first measuring unit, the second measuring unit and the sample transport unit, the respective control substrates are connected to the information processing unit so as to communicate therewith and the control substrates control the first measuring unit, the second measuring unit and the sample transport unit, respectively in accordance with a command transmitted from the information processing unit.

In addition, in the above-described embodiment, the configuration has been described in which the sample analyzer includes the information processing unit which is provided independently of the first measuring unit and the second measuring unit, but the invention is not limited thereto. The sample analyzer may be an integrated sample analyzer equipped with the measuring units and the information processing unit in a single casing.

In addition, in the above-described embodiment, the example is shown in which the invention is applied to a multiple blood cell analyzer, but the invention is not limited thereto. The invention may be applied to a sample analyzer other than the multiple blood cell analyzer, such as a blood coagulation measurement device, an immunological analyzer, an in-urine physical component analyzer, an urine qualitative analyzer or a biochemical analyzer, which analyzes a sample by using a plural kinds of reagents. In this case, a reagent container which is installed in the reagent container installation section is not limited to a reagent container containing a staining liquid for blood cell analysis. In the case of a blood coagulation measurement device, a reagent container containing a reagent for blood coagulation measurement may be installed in the reagent container installation section. In the case of an in-urine physical component analyzer, a reagent container containing a reagent for in-urine physical component analysis may be installed in the reagent container installation section. In the case of a urine qualitative analyzer, a reagent container containing a reagent for urine qualitative analysis may be installed in the reagent container installation section. In the case of a biochemical analyzer, a reagent container containing a reagent for biochemical analysis may be installed in the reagent container installation section. In the case of an immunological analyzer, a reagent container containing a reagent for immunological analysis may be installed in the reagent container installation section. In addition, a configuration may also be provided in which a reagent container containing a reagent other than a staining liquid for blood cell analysis, for example, a hemolytic agent is installed in the reagent container installation section in the multiple blood cell analyzer.

In addition, in the above-described embodiment, the configuration has been described in which the single computer 5a executes all the processes of the computer program 54a, but the invention is not limited thereto. The same process as the above-described computer program 54a may be dispersed to a plurality of devices (computers) and executed.

INDUSTRIAL APPLICABILITY

The sample analyzer of the invention is useful as a sample analyzer which analyzes a sample by using a reagent.

What is claimed is:

1. A sample analyzer comprising:
a container set section configured to receive a reagent container inside which contains a reagent of a selected type to be used in a sample analysis;
a specimen preparing section configured to prepare a measurement specimen from the reagent and a sample;
a measurement section configured to measure the measurement specimen;
a cover which is provided in the container set section, the cover moves to an open position where the setting of the reagent container in the container set section is permitted and a closed position where the setting of the reagent container in the container set section is not permitted;
a locking section operable to lock the cover in the open position for replacement of the reagent in the container set section and to release the cover after replacement of the reagent container so that the cover becomes movable to the closed position;
a reader operable to read reagent information of a reagent in a reagent container form an information recording medium attached to the reagent container received in the container set section; and
a controller comprising a processor and a memory that stores a program to be executed by the processor to:
operate the locking section to lock the cover in the open position during replacement of the reagent container in the container set section with a new reagent container;
while the cover remains locked in the open position, operate the reader to read reagent information on a reagent contained in the new reagent container received in the container set section;
while the cover remains locked in the open position, determine, based on the reagent information read by the reader, whether the reagent in the new reagent container is of the selected type;
operate the locking section to unlock the cover if the reagent in the new reagent container is determined to be of the selected type so that the cover becomes movable to the closed position; and
leave the cover locked in the open position if the reagent in the new reagent container is determined not of the selected type.

2. The sample analyzer according to claim 1, further comprising a detector that detects an opening of the cover,
wherein the controller is programmed by stored program to operate the locking section to lock the cover open if the detector detects the opening of the cover and leave the cover locked open until the controller determines that the reagent in the new regent container is of the selected type.

3. The sample analyzer according to claim 2,
wherein the controller is programmed by the stored program to determine, if the detector detects the opening of the cover, whether the container set section is identified as having a depleting reagent container to be replaced, and operate the locking section to lock the cover open if the controller determines that the container set section is identified as having a depleting reagent container to be replaced.

4. The sample analyzer according to claim 1, further comprising a display,
wherein the controller is programmed by the stored program to display on the display, if the controller determines that the reagent in the new reagent container of the selected type, a notification for prompting a user to close the cover.

5. The sample analyzer according to claim 1, further comprising a display,
wherein the controller is programmed by the stored program to display on the display, if the controller determines that the reagent in the new reagent container is not of the selected type, a notification for prompting a user to set a reagent container with the reagent of the selected type in the container set section.

6. The sample analyzer according to claim 1, wherein the reagent information includes at least one of type information indicating a type of the reagent contained in the reagent container, remaining amount information indicating an amount of the reagent remaining in the reagent container, and expiration date information indicating an expiration date of the reagent.

7. The sample analyzer according to claim 1,
wherein the controller is programmed by the stored program to operate the locking section to lock the cover closed and leave the cover locked closed during the sample analysis to prevent an accidental removal or replacement of the reagent container in the container set section.

8. The sample analyzer according to claim 1, further comprising an open/close switch for manually opening or closing the cover,
wherein the controller is programmed by the stored program to respond to an operation of the open/close switch to operate the locking section to unlock the cover so that the cover becomes movable to close the container set section if the open/close switch is operated when the cover is locked open.

9. The sample analyzer according to claim 1, comprising:
a plurality of other container set sections; and
a plurality of other covers provided, respectively, with the other container set sections to open and close the other container set sections.

10. The sample analyzer according to claim 1, further comprising a piercer configured to suction the reagent from the reagent container received in the container set section; and
a piercer lifting mechanism configured to move the piercer in response to an opening and a closing of the cover so that the piercer retreats from the reagent container when the cover is being opened and advances into the reagent container when the cover is being closed.

11. The sample analyzer according to claim 10,
wherein the reagent container includes a lid formed puncturable by the piercer, and
the piercer lifting mechanism operable to move the piercer so that the piercer punctures the lid and advances into the reagent container when the cover is being closed.

12. The sample analyzer according to claim 1,
wherein the controller is programmed by the stored program to detect an amount of reagent left in the reagent container and determine from the detected amount whether a replacement of the reagent container is needed.

13. The sample analyzer according to claim 1,
wherein the reagent container contains a staining liquid for staining the blood cell.

14. The sample analyzer according to claim 1, wherein the locking section comprises a solenoid that comprises a plunger, and the solenoid, responsive to a supply of current to the solenoid, extends the plunger away from the solenoid so that the plunger engages the cover to lock the cover open or closed.

15. The sample analyzer according to claim 14, wherein the cover is formed with a first locking hole and a second locking hole, and the cover is locked open when the extending plunger engages the first locking hole and locked closed when the extending plunger engages the second locking hole.

* * * * *

UNITED STATES PATENT AND TRADEMARK OFFICE
CERTIFICATE OF CORRECTION

PATENT NO. : 8,968,656 B2  
APPLICATION NO. : 13/074490  
DATED : March 3, 2015  
INVENTOR(S) : Yuichi Hamada It is certified that error appears in the above-identified patent and that said Letters Patent is hereby corrected as shown below:

In the Claims

In column 25, claim 2, line 44, after "is programmed by" insert --the--.

Signed and Sealed this  
Twenty-second Day of September, 2015

Michelle K. Lee  
*Director of the United States Patent and Trademark Office*